United States Patent
Oh et al.

(10) Patent No.: US 10,400,020 B2
(45) Date of Patent: Sep. 3, 2019

(54) LONG-ACTING CONJUGATE OF TRIPLE GLUCAGON/GLP-1/GIP RECEPTOR AGONIST

(71) Applicant: HANMI PHARM. CO., LTD., Hwaseong-si, Gyeonggi-do (KR)

(72) Inventors: Euh Lim Oh, Hwaseong-si (KR); Jong Suk Lee, Hwaseong-si (KR); Young Jin Park, Hwaseong-si (KR); Chang Ki Lim, Hwaseong-si (KR); Sung Youb Jung, Hwaseong-si (KR); Se Chang Kwon, Hwaseong-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 0 days.

(21) Appl. No.: 16/024,014

(22) Filed: Jun. 29, 2018

(65) Prior Publication Data

US 2018/0311315 A1  Nov. 1, 2018

Related U.S. Application Data

(63) Continuation of application No. PCT/KR2016/015555, filed on Dec. 30, 2016.

(30) Foreign Application Priority Data

Dec. 31, 2015  (KR) .................. 10-2015-0191082
Dec. 2, 2016  (KR) .................. 10-2016-0163737

(51) Int. Cl.
| | | |
|---|---|---|
| A61K 38/00 | (2006.01) |
| C07K 14/605 | (2006.01) |
| A61K 38/26 | (2006.01) |
| A61K 39/395 | (2006.01) |
| A61P 3/04 | (2006.01) |
| A61P 3/10 | (2006.01) |
| C07K 16/28 | (2006.01) |
| C07K 14/47 | (2006.01) |
| A61P 9/12 | (2006.01) |
| A61K 47/60 | (2017.01) |
| A61P 9/10 | (2006.01) |

(52) U.S. Cl.
CPC ............ C07K 14/605 (2013.01); A61K 38/26 (2013.01); A61K 39/3955 (2013.01); A61P 3/04 (2018.01); A61P 3/10 (2018.01); C07K 14/47 (2013.01); C07K 16/283 (2013.01); A61K 38/00 (2013.01); A61K 47/60 (2017.08); A61P 9/10 (2018.01); A61P 9/12 (2018.01)

(58) Field of Classification Search
None
See application file for complete search history.

(56) References Cited

U.S. PATENT DOCUMENTS

| | | | |
|---|---|---|---|
| 5,408,037 A | 4/1995 | Smith et al. | |
| 7,994,122 B2 | 8/2011 | Riber et al. | |
| 8,450,270 B2 | 5/2013 | DiMarchi et al. | |
| 8,454,971 B2 | 6/2013 | Day et al. | |
| 8,507,428 B2 | 8/2013 | DiMarchi et al. | |
| 8,703,701 B2 | 4/2014 | DiMarchi | |
| 2010/0105877 A1 | 4/2010 | Song et al. | |
| 2010/0190699 A1 | 7/2010 | DiMarchi et al. | |
| 2011/0082079 A1 | 4/2011 | Spetzler et al. | |
| 2012/0288511 A1 | 11/2012 | DiMarchi | |
| 2012/0329715 A1 | 12/2012 | Greig et al. | |
| 2013/0116173 A1 | 5/2013 | DiMarchi et al. | |
| 2013/0143798 A1 | 6/2013 | Lau et al. | |
| 2013/0203659 A1* | 8/2013 | Miranda .............. | C07K 14/605 514/5.3 |
| 2014/0011738 A1 | 1/2014 | DiMarchi | |
| 2015/0368310 A1 | 12/2015 | DiMarchi et al. | |
| 2018/0311315 A1 | 11/2018 | Oh et al. | |

FOREIGN PATENT DOCUMENTS

| | | |
|---|---|---|
| JP | 5476304 B2 | 2/2014 |
| KR | 10-2009-0096498 A | 9/2009 |
| KR | 10-2012-0010146 A | 2/2012 |
| KR | 10-2012-0052973 A | 5/2012 |
| KR | 10-2013-0018410 A | 2/2013 |
| KR | 10-2014-0018462 A | 2/2014 |
| KR | 10-1382593 B1 | 4/2014 |
| KR | 1020150096398 A | 8/2015 |
| KR | 1020150096433 A | 8/2015 |
| WO | 96/16196 A2 | 5/1996 |
| WO | 96/16196 A3 | 5/1996 |
| WO | 96/32478 A1 | 10/1996 |
| WO | 97/34631 A1 | 9/1997 |
| WO | 2004/093823 A2 | 11/2004 |
| WO | 2010/011439 A2 | 1/2010 |
| WO | 2010/096052 A1 | 8/2010 |
| WO | 2011/075393 | 6/2011 |
| WO | 2011/117415 A1 | 9/2011 |

(Continued)

OTHER PUBLICATIONS

Korean Intellectual Property Office, Communication dated Jul. 11, 2018, issued in corresponding Korean Application No. 10-2016-0183500.

Australian Patent Office, Communication dated Jul. 31, 2018, issued in corresponding Australian Application No. 2016382394.

Daniel J. Drucker, et al., "The Incretin system: glucagon-like peptide-1 receptor agonists and dipeptidyl peptidase-4 inhibitors in type 2 diabetes", The Lancet, New Drug Class, Nov. 2006, pp. 1696-1705, vol. 368, No. 11.

Yahiya Y. Syed, et al., "Exenatide Extended-Release: An Updated Review of Its Use in Type 2 Diabetes Mellitus", Drugs, Jun. 2015, 12 pages, vol. 10.

(Continued)

*Primary Examiner* — Jeanette M Lieb
(74) *Attorney, Agent, or Firm* — Sughrue Mion, PLLC

(57) ABSTRACT

The present invention relates to a long-acting conjugate of a triple agonist having activities to all of glucagon, GLP-1, and GIP receptors and uses thereof.

24 Claims, 2 Drawing Sheets

Specification includes a Sequence Listing.

(56) References Cited

FOREIGN PATENT DOCUMENTS

| | | |
|---|---|---|
| WO | 2012/011752 A2 | 1/2012 |
| WO | 2012088116 A1 | 6/2012 |
| WO | 2012/158965 A2 | 11/2012 |
| WO | 2012/169798 A2 | 12/2012 |
| WO | 2012/173422 A1 | 12/2012 |
| WO | 2013/004983 A1 | 1/2013 |
| WO | 2013/074910 A1 | 5/2013 |
| WO | 2013192129 A1 | 12/2013 |
| WO | 2013192130 A1 | 12/2013 |
| WO | 2014/017843 A1 | 1/2014 |
| WO | 2014/073842 A1 | 5/2014 |
| WO | 2014/073845 A1 | 5/2014 |
| WO | 2014/081864 A1 | 5/2014 |
| WO | 2014/081872 A1 | 5/2014 |
| WO | 2014/096150 | 6/2014 |
| WO | 2014/170496 A1 | 10/2014 |
| WO | 2016049190 A1 | 3/2016 |
| WO | 2016/108586 A1 | 7/2016 |
| WO | 2017/003191 A1 | 1/2017 |

OTHER PUBLICATIONS

Jonathan W. Day, et al., "A new glucagon and GLP-1 co-agonist eliminates obesity in rodents", Nature Chemical Biology, Oct. 2009, pp. 749-757, vol. 5, No. 10.

Brian Finan, et al., "A rationally designed monomeric peptide triagonist corrects obesity and diabetes in rodents", Nature Medicine, Jan. 2015, 1-13 pages, vol. 21, No. 1.

International Searching Authority, International Search Report for PCT/KR2016/015555 dated Apr. 10, 2017 [PCT/ISA/210].

International Searching Authority, International Search Report for PCT/KR2016/015554 dated Apr. 10, 2017 [PCT/ISA/210].

Korean Intellectual Property Office, Communication dated Jul. 11, 2018, issued in Korean Application No. 10-2016-0183499.

Australian Patent Office, Communication dated Jul. 31, 2018, issued in Australian Application No. 2016382393.

U.S. Appl. No. 16/263,469, Euh Lim Oh, filed Jan. 31, 2019.

U.S. Appl. No. 16/023,994, Euh Lim Oh, filed Jun. 29, 2018.

U.S. Appl. No. 15/540,729, Jung Kuk Kim, filed Jun. 29, 2017.

U.S. Appl. No. 15/740,668, Jung Kuk Kim, filed Dec. 28, 2017.

U.S. Appl. No. 16/233,890, Jung Kuk Kim, filed Dec. 27, 2018.

Ecuador Patent Office; Communication dated Feb. 3, 2019 in application No. SENADI-2018- 53053.

Ecuador Patent Office; Communication dated Feb. 3, 2019 in application No. SENADI-2018- 53055.

Colombia Patent Office; Communication dated Jul. 17, 2018 in application No. NC2017/0006308.

European Patent Office; Communication dated Jun. 12, 2018 in application No. 15875680.9.

"Calculating approximate isoelectric points for amino acids and peptides", Nov. 1, 2011, pp. 1-2, XP055471990, Retrieved from the Internet: URL:http://www.elcamino.edu/faculty/pdoucette/calculating-approximate-isoelectric-points.pdf (2 pages total).

Joseph Chabenne et al., "A glucagon analog chemically stabilized for immediate treatment of life-threatening hypoglycemia," Molecular Metabolism, Jan. 2014, pp. 293-300, vol. 3.

Kevin L. Shaw et al., "The effect of net charge on the solubility, activity, and stability of ribonuclease Sa," Protein Science, 2001, pp. 1206-1215, vol. 10 (11 pages total).

International Searching Authority; International Search Report for PCT/KR2015/014422 dated Apr. 14, 2016 (PCT/ISA/210).

Korean Intellectual Property Office; Communication dated Jul. 12, 2018 in application No. 10-2016-0081976.

John Eng et al., "Isolation and Characterization of Exendin-4, an Exendin-3 Analogue, from *Heloderma suspectum* Venom", The Journal of Biological Chemistry, vol. 267, No. 11 Apr. 15, 1992, pp. 7402-7405.

Elisabeth Gasteiger et al., "ExPASy: the proteomics server for in-depth protein knowledge and analysis", Nucleic Acids Research, 2003, pp. 3784-3788. vol. 31, No. 13, 2003.

International Searching Authority; Written Opinion for PCT/KR2016/006984, dated Sep. 12, 2016 (PCT/ISA/237).

International Searching Authority; International Search Report for PCT/KR2016/006984, dated Sep. 12, 2016 (PSA/ISA/210).

International Searching Authority; International Search Report for PCT/KR2017/006922 dated Dec. 7, 2017 (PCT/ISA/210).

United States Patent and Trademark Office; Communication dated Feb. 27, 2019, issued in U.S. Appl. No. 16/023,994.

Ecuador Patent Office; Communication dated Feb. 3, 2018 in counterpart EC application No. IEPI-2018-3879.

Cecilia G. Unson et al., "The Role of Histidine-1 in Glucagon Action", Archives of Biochemistry and Biophysics, vol. 300, No. 2, Feb. 1, 1993, pp. 747-750 (6 pages total), CAplus accession No. DN 118:205395.

Australian Patent Office; Communication dated Feb. 7, 2019 in counterpart application No. 2017289014.

\* cited by examiner

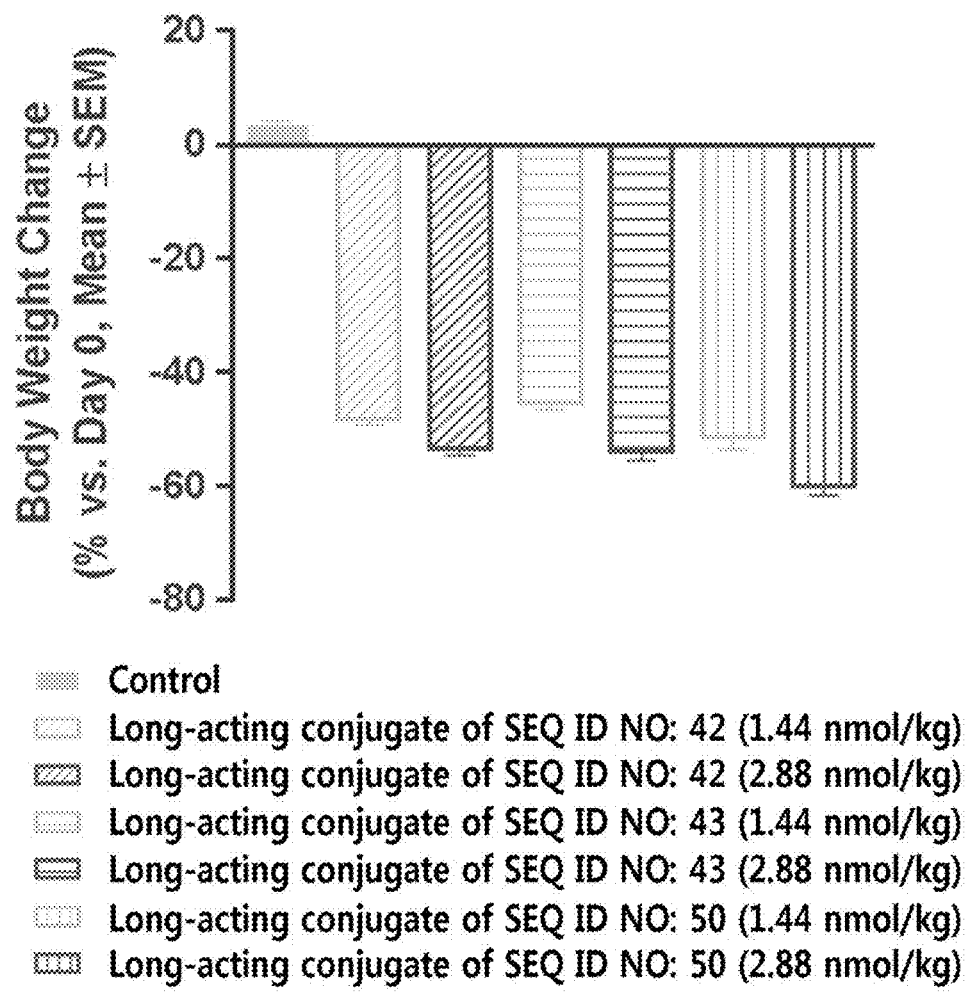
[FIG. 1]

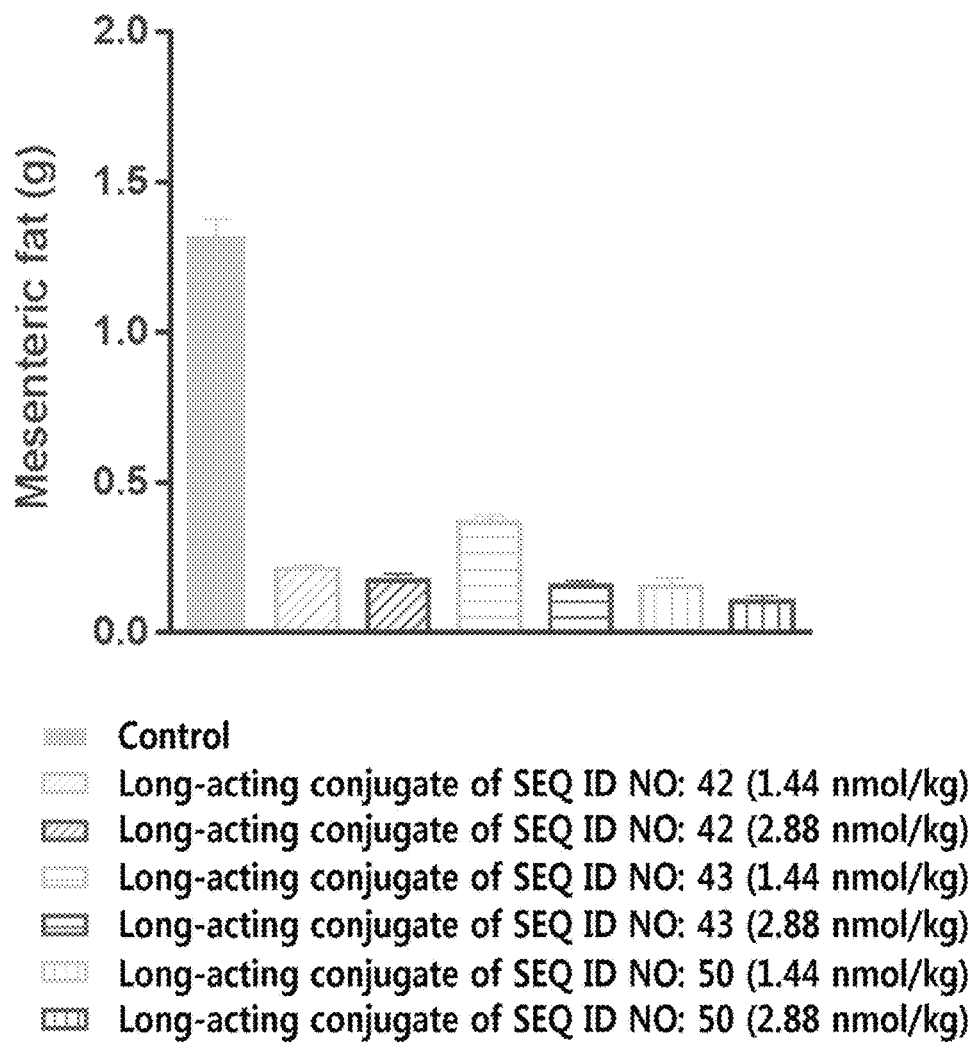
[FIG. 2]

LONG-ACTING CONJUGATE OF TRIPLE GLUCAGON/GLP-1/GIP RECEPTOR AGONIST

CROSS REFERENCE TO RELATED APPLICATIONS

This is a bypass continuation of Application No. PCT/KR2016/015555 filed Dec. 30, 2016, which claims priority from Korean Patent Application Nos. KR 10-2016-0163737 filed Dec. 2, 2016 and KR 10-2015-0191082 filed Dec. 31, 2015, of which entire disclosures are hereby incorporated by reference.

TECHNICAL FIELD

The present invention relates to a long-acting conjugate of a triple agonist having activities to all of glucagon, GLP-1, and GIP receptors, and uses thereof.

BACKGROUND ART

Obesity and diabetes including type 2 diabetes are representative metabolic diseases that occur in modern society. These diseases are regarded as health-threatening factors in the world and the accompanying economic costs due to the incidence of these diseases are rapidly increasing at present.

Glucagon-like peptide-1 (GLP-1) and glucose-dependent insulinotropic polypeptide (GIP) are representative gastrointestinal hormones and neuronal hormones and are materials involved in the control of blood glucose levels according to food intake. Glucagon is a peptide hormone secreted by the pancreas and is involved in controlling the blood glucose levels along with the two materials described above.

GLP-1 is a hormone secreted by the small intestine stimulated by food intake. GLP-1 promotes insulin secretion in the pancreas in a blood glucose-dependent manner and inhibits the secretion of glucagon, thus helping the action of lowering blood glucose levels. Additionally, GLP-1 has the roles of slowing digestive action in the gastrointestinal tract by acting as a satiety factor, and reducing the amount of food intake by delaying the time for emptying digested food in the gastrointestinal tract. Furthermore, the administration of GLP-1 to rats was reported to have effects of inhibiting food intake and reducing body weight, and these effects were confirmed to occur equally both in normal and obese states, thus showing the potential of GLP-1 as an agent for treating obesity.

GIP, one of the gastrointestinal hormones secreted by the stimulation of food intake as is the case of GLP-1, is a hormone consisting of 42 amino acids secreted by the intestinal K-cells. GIP was reported to perform the functions of promoting the secretion of insulin in the pancreas in a blood glucose-dependent manner and helping to lower the blood glucose levels, thereby exhibiting the effects of increasing the activation of GLP-1, anti-inflammation, etc.

Glucagon is produced in the pancreas when the blood glucose levels fall due to reasons such as medications, diseases, deficiency in hormones or enzymes, etc. Glucagon sends a signal for glycogen breakdown in the liver to induce the release of glucose and increases blood glucose levels to a normal level. In addition to the effect of increasing the blood glucose levels, glucagon suppresses appetite in animals and humans and activates hormone-sensitive lipase of adipocytes to promote lipolysis and energy expenditure, thereby showing an anti-obesity effect.

As such, active studies are being conducted to develop GLP-1 as a therapeutic agent for treating diabetes and obesity, based on the effects of GLP-1 controlling blood glucose levels and reducing body weight. Currently, exendin-4, prepared from lizard venom and having an amino acid homology of about 50% with GLP-1, is under development as a therapeutic agent for treating the same kinds of diseases. However, the therapeutic agents containing GLP-1 and exendin-4 were reported to show side-effects such as vomiting and nausea (Syed Y Y., Drugs, 2015 July; 75 (10): 1141-52).

Additionally, for the maximization of body weight reduction and as an alternative to the above-described GLP-1-based therapeutic material, studies have been focused on dual agonists having activities to both GLP-1 receptors and glucagon receptors, and they were shown to be more effective in body weight reduction due to the activation of glucagon receptors, compared to when the existing GLP-1 was treated alone (Jonathan W et al., Nat Chem Bio., 2009 October (5); 749-757).

Additionally, in the study related to triple agonists, which have activities to all of GLP-1, GIP, and glucagon receptors simultaneously, efforts have been made recently to increase the half-life of the triple agonists by substituting an amino acid sequence to increase the resistance to dipeptidyl peptidase-IV (DPP-IV), which decomposes gastrointestinal hormones to get rid of their activities, followed by adding an acyl group to a particular region thereof (Finan B et al., Nat Med., 2015 January; 21 (1): 27-36). However, their effects of activating three different kinds of receptors were not significant and no triple agonist showed various active ratios thereto.

Accordingly, there is a need for the development of a novel material which can highly activate GLP-1, GIP, and glucagon receptors and has the effects of controlling blood glucose levels and reducing body weight without causing any side-effects such as vomiting and nausea.

Additionally, there is also a need for the development of a novel material which has various active ratios to GLP-1, GIP, and glucagon receptors. For example, there is an increasing need for the development of a material which has an effect of reducing body weight but has a significantly higher effect of controlling blood glucose levels due to high GLP-1 and GIP activities but with relatively low glucagon activity for a hypoglycemic effect; or a material which has high activities for all of GLP-1, GIP, and glucagon, thus having a significantly high effect of reducing body weight.

Additionally, GLP-1, GIP, and glucagon have low in vivo stability and thus they have a disadvantage in that they must be administered daily or twice daily when they are applied to humans for therapeutic uses.

DISCLOSURE

Technical Problem

An object of the present invention is to provide a conjugate of a peptide having activities to a glucagon receptor, a glucagon-like peptide-1 (GLP-1) receptor, and a glucose-dependent insulinotropic polypeptide (GIP) receptor.

Another object of the present invention is to provide a polynucleotide encoding the conjugate, a vector including the polynucleotide, and a transformant including the polynucleotide or the vector.

Still another object of the present invention is to provide a composition containing the conjugate.

Still another object of the present invention is to provide a method for treating a target disease, which includes administering the conjugate or a composition containing the conjugate to a subject in need thereof.

Still another object of the present invention is to provide a use of the conjugate or composition thereof for use in the preparation of a medicament.

Technical Solution

To achieve the above objects, in an aspect, the present invention provides a conjugate of a peptide having activities to a glucagon receptor, a glucagon-like peptide-1 (GLP-1) receptor, and a glucose-dependent insulinotropic polypeptide (GIP) receptor.

In a specific embodiment, the conjugate is represented by Chemical Formula 1 below:

X-La-F            [Chemical Formula 1]

wherein,

X is a peptide having activities to a glucagon receptor, a glucagon-like peptide-1 (GLP-1) receptor, and a glucose-dependent insulinotropic polypeptide (GIP) receptor;

L is a linker;

a is 0 or a positive integer, with the proviso that when a is 2 or greater, each L is independent from each other; and F is a material capable of increasing the half-life of X.

In another specific embodiment, X is an analog of native glucagon with a variation selected from the group consisting of substitution, addition, deletion, modification, and a combination thereof, on at least one amino acid of the native glucagon sequence.

In still another specific embodiment, the amino acid sequence with addition is derived from a native GLP-1 amino acid sequence, a native GIP amino acid sequence, or a native exendin-4 amino acid sequence.

In still another specific embodiment, the X is a peptide including an amino acid sequence represented by General Formula 1 below:

```
                 (General Formula 1, SEQ ID NO: 103)
Xaa1-Xaa2-Xaa3-Gly-Thr-Phe-Xaa7-Ser-Asp-Xaa10-Ser- Xaa12-Xaa13-Xaa14-Xaa15-Xaa16-Xaa17-Xaa18-Xaa19-

Xaa20-Xaa21-Phe-Xaa23-Xaa24-Trp-Leu-Xaa27-Xaa28-

Xaa29-Xaa30-R1
``` wherein, in General Formula 1,

Xaa1 is histidine (His, H), 4-imidazoacetyl (CA), or tyrosine (Tyr, Y);

Xaa2 is glycine (Gly, G), α-methyl-glutamic acid, or Aib (aminoisobutyric acid);

Xaa3 is glutamic acid (Glu, E) or glutamine (Gln, Q);

Xaa7 is threonine (Thr, T) or isoleucine (Ile, I);

Xaa10 is leucine (Leu, L), tyrosine (Tyr, Y), lysine (Lys, K), cysteine (Cys, C), or valine (Val, V);

Xaa12 is lysine (Lys, K), serine (Ser, S), or isoleucine (Ile, I);

Xaa13 is glutamine (Gln, Q), tyrosine (Tyr, Y), alanine (Ala, A), or cysteine (Cys, C);

Xaa14 is leucine (Leu, L), methionine (Met, M), or tyrosine (Tyr, Y);

Xaa15 is cysteine (Cys, C), aspartic acid (Asp, D), glutamic acid (Glu, E), or leucine (Leu, L);

Xaa16 is glycine (Gly, G), glutamic acid (Glu, E), or serine (Ser, S);

Xaa17 is glutamine (Gln, Q), arginine (Arg, R), isoleucine (Ile, I), glutamic acid (Glu, E), cysteine (Cys, C), or lysine (Lys, K);

Xaa18 is alanine (Ala, A), glutamine (Gln, Q), arginine (Arg, R), or histidine (His, H);

Xaa19 is alanine (Ala, A), glutamine (Gln, Q), cysteine (Cys, C), or valine (Val, V);

Xaa20 is lysine (Lys, K), glutamine (Gln, Q), or arginine (Arg, R);

Xaa21 is glutamic acid (Glu, E), glutamine (Gln, Q), leucine (Leu, L), cysteine (Cys, C), or aspartic acid (Asp, D);

Xaa23 is isoleucine (Ile, I) or valine (Val, V);

Xaa24 is alanine (Ala, A), glutamine (Gln, Q), cysteine (Cys, C), asparagine (Asn, N), aspartic acid (Asp, D), or glutamic acid (Glu, E);

Xaa27 is valine (Val, V), leucine (Leu, L), lysine (Lys, K), or methionine (Met, M);

Xaa28 is cysteine (Cys, C), lysine (Lys, K), alanine (Ala, A), asparagine (Asn, N), or aspartic acid (Asp, D);

Xaa29 is cysteine (Cys, C), glycine (Gly, G), glutamine (Gln, Q), threonine (Thr, T), glutamic acid (Glu, E), or histidine (His, H);

Xaa30 is cysteine (Cys, C), glycine (Gly, G), lysine (Lys, K), or histidine (His, H), or is absent; and R1 is cysteine (Cys, C), GKKNDWKHNIT (SEQ ID NO: 106), m-SSGAPPPS-n (SEQ ID NO: 107), or m-SSGQP-PPS-n (SEQ ID NO: 108), or is absent;

wherein, m is -Cys-, -Pro-, or -Gly-Pro-, n is -Cys-, -Gly-, -Ser-, or -His-Gly-, or is absent.

In still another specific embodiment, in General Formula 1,

Xaa14 is leucine or methionine; and

Xaa15 is cysteine, aspartic acid, or leucine.

In still another specific embodiment, in General Formula 1,

Xaa2 is glycine, α-methyl-glutamic acid, or Aib;

Xaa7 is threonine;

Xaa10 is tyrosine, cysteine, or valine;

Xaa12 is lysine or isoleucine;

Xaa13 is tyrosine, alanine, glutamine, or cysteine;

Xaa14 is leucine, cysteine, or methionine;

Xaa15 is cysteine, leucine, glutamic acid, or aspartic acid;

Xaa17 is glutamine, arginine, isoleucine, cysteine, glutamic acid, or lysine;

Xaa18 is alanine, glutamine, arginine, or histidine;

Xaa19 is alanine, glutamine, valine, or cysteine;

Xaa20 is lysine, arginine, or glutamine;

Xaa21 is glutamic acid, glutamine, leucine, cysteine, or aspartic acid;

Xaa23 is isoleucine or valine;

Xaa24 is cysteine, alanine, glutamine, asparagine, glutamic acid, or aspartic acid; and Xaa27 is leucine or lysine.

In still another specific embodiment, in General Formula 1,

Xaa2 is glycine, α-methyl-glutamic acid, or Aib;

Xaa7 is threonine;

Xaa10 is tyrosine, cysteine, or valine;

Xaa12 is lysine or isoleucine;

Xaa13 is tyrosine, alanine, or cysteine;

Xaa14 is leucine or methionine;

Xaa15 is cysteine or aspartic acid;

Xaa17 is glutamine, arginine, isoleucine, cysteine, or lysine;

Xaa18 is alanine, arginine, or histidine;

Xaa19 is alanine, glutamine, or cysteine;
Xaa20 is lysine or glutamine;
Xaa21 is glutamic acid, cysteine, or aspartic acid;
Xaa23 is valine;
Xaa24 is alanine, glutamine, cysteine, asparagine, or aspartic acid; and
Xaa27 is leucine or lysine.

In still another specific embodiment, in General Formula 1,
Xaa2 is α-methyl-glutamic acid or Aib;
Xaa7 is threonine;
Xaa10 is tyrosine or cysteine;
Xaa12 is lysine or isoleucine;
Xaa13 is tyrosine, alanine, or cysteine;
Xaa14 is leucine or methionine;
Xaa15 is cysteine or aspartic acid;
Xaa16 is glutamic acid;
Xaa17 is arginine, isoleucine, cysteine, or lysine;
Xaa18 is alanine, arginine, or histidine;
Xaa19 is alanine, glutamine, or cysteine;
Xaa20 is lysine or glutamine;
Xaa21 is glutamic acid or aspartic acid;
Xaa23 is valine;
Xaa24 is glutamine, asparagine, or aspartic acid;
Xaa27 is leucine; and
Xaa28 is cysteine, alanine, asparagine, or aspartic acid.

In still another specific embodiment, in General Formula 1,
Xaa1 is histidine or 4-imidazoacetyl;
Xaa2 is α-methyl-glutamic acid or Aib;
Xaa3 is glutamine;
Xaa7 is threonine;
Xaa10 is tyrosine;
Xaa12 is isoleucine;
Xaa13 is alanine or cysteine;
Xaa14 is methionine;
Xaa15 is aspartic acid;
Xaa16 is glutamic acid;
Xaa17 is isoleucine or lysine;
Xaa18 is alanine or histidine;
Xaa19 is glutamine or cysteine;
Xaa20 is lysine;
Xaa21 is aspartic acid;
Xaa23 is valine;
Xaa24 is asparagine;
Xaa27 is leucine;
Xaa28 is alanine or asparagine;
Xaa29 is glutamine or threonine; and
Xaa30 is cysteine, or lysine, or is absent.

In still another specific embodiment, in General Formula 1,
Xaa2 is glycine, α-methyl-glutamic acid, or Aib;
Xaa3 is glutamine;
Xaa7 is threonine;
Xaa10 is tyrosine, cysteine, or valine;
Xaa12 is lysine;
Xaa13 is tyrosine;
Xaa14 is leucine;
Xaa15 is aspartic acid;
Xaa16 is glycine, glutamic acid, or serine;
Xaa17 is glutamine, arginine, cysteine, or lysine;
Xaa18 is alanine, arginine, or histidine;
Xaa19 is alanine or glutamine;
Xaa20 is lysine or glutamine;
Xaa21 is glutamic acid, cysteine, or aspartic acid;
Xaa23 is valine;
Xaa24 is alanine, glutamine, or cysteine;
Xaa27 is leucine or lysine; and
Xaa29 is glycine, glutamine, threonine, or histidine.

In still another specific embodiment, X is a peptide including an amino acid sequence represented by General Formula 2 below:

```
                       (General Formula 2, SEQ ID NO: 104)
Xaa1-Xaa2-Gln-Gly-Thr-Phe-Thr-Ser-Asp-Xaa10-Ser- Lys-Xaa13-Xaa14-Xaa15-Xaa16-Xaa17-Xaa18-Xaa19-

Xaa20-Xaa21-Phe-Xaa23-Xaa24-Trp-Leu-Leu-Xaa28-

Xaa29-Xaa30-Xaa31-Ser-Ser-Gly-Gln-Pro-Pro-Pro-

Ser-Xaa40
```

In General Formula 2,
Xaa1 is 4-imidazoacetyl, histidine, or tyrosine;
Xaa2 is glycine, α-methyl-glutamic acid, or Aib;
Xaa10 is tyrosine or cysteine;
Xaa13 is alanine, glutamine, tyrosine, or cysteine;
Xaa14 is leucine, methionine, or tyrosine;
Xaa15 is aspartic acid, glutamic acid, or leucine;
Xaa16 is glycine, glutamic acid, or serine;
Xaa17 is glutamine, arginine, isoleucine, glutamic acid, cysteine, or lysine;
Xaa18 is alanine, glutamine, arginine, or histidine;
Xaa19 is alanine, glutamine, cysteine, or valine;
Xaa20 is lysine, glutamine, or arginine;
Xaa21 is cysteine, glutamic acid, glutamine, leucine, or aspartic acid;
Xaa23 is isoleucine or valine;
Xaa24 is cysteine, alanine, glutamine, asparagine, or glutamic acid;
Xaa28 is lysine, cysteine, asparagine, or aspartic acid;
Xaa29 is glycine, glutamine, cysteine, or histidine;
Xaa30 is cysteine, glycine, lysine, or histidine;
Xaa31 is proline or cysteine; and
Xaa40 is cysteine or is absent.

In still another specific embodiment, in General Formula 2,
Xaa13 is alanine, tyrosine, or cysteine;
Xaa15 is aspartic acid or glutamic acid;
Xaa17 is glutamine, arginine, cysteine, or lysine;
Xaa18 is alanine, arginine, or histidine;
Xaa21 is cysteine, glutamic acid, glutamine, or aspartic acid;
Xaa23 is isoleucine or valine;
Xaa24 is cysteine, glutamine, or asparagine;
Xaa28 is cysteine, asparagine, or aspartic acid;
Xaa29 is glutamine, cysteine, or histidine; and
Xaa30 is cysteine, lysine, or histidine.

In still another specific embodiment, X is a peptide including an amino acid sequence represented by General Formula 3 below:

```
                       (General Formula 3, SEQ ID NO: 105)
Xaa1-Xaa2-Gln-Gly-Thr-Phe-Thr-Ser-Asp-Tyr-Ser-Lys- Xaa13-Leu-Asp-Glu-Xaa17-Xaa18-Xaa19-Lys-Xaa21-Phe- Val-Xaa24-Trp-Leu-Leu-Xaa28-Xaa29-Xaa30-Xaa31-Ser- Ser-Gly-Gln-Pro-Pro-Pro-Ser-Xaa40.
```

In General Formula 3,
Xaa1 is histidine or tyrosine;
Xaa2 is α-methyl-glutamic acid or Aib;

Xaa13 is alanine, tyrosine, or cysteine;
Xaa17 is arginine, cysteine, or lysine;
Xaa18 is alanine or arginine;
Xaa19 is alanine or cysteine;
Xaa21 is glutamic acid or aspartic acid;
Xaa24 is glutamine or asparagine;
Xaa28 is cysteine or aspartic acid;
Xaa29 is cysteine, histidine, or glutamine;
Xaa30 is cysteine or histidine;
Xaa31 is proline or cysteine; and
Xaa40 is cysteine or is absent.

In still another specific embodiment, R1 is cysteine, GKKNDWKHNIT (SEQ ID NO: 106), CSSGQPPPS (SEQ ID NO: 109), GPSSGAPPPS (SEQ ID NO: 110), GPSSGAPPPSC (SEQ ID NO: 111), PSSGAPPPS (SEQ ID NO: 112), PSSGAPPPSG (SEQ ID NO: 113), PSSGAPPPSHG (SEQ ID NO: 114), PSSGAPPPSS (SEQ ID NO: 115), PSSGQPPPS (SEQ ID NO: 116), or PSSGQPPPSC (SEQ ID NO: 117), or is absent.

In still another specific embodiment, in General Formulas 1 to 3, the $16^{th}$ amino acid and the $20^{th}$ amino acid from the N-terminus together form a ring.

In still another specific embodiment, X is a peptide including an amino acid sequence selected from the group consisting of SEQ ID NOS: 1 to 102.

In still another specific embodiment, F is selected from the group consisting of a polymer, fatty acid, cholesterol, albumin and a fragment thereof, an albumin-binding material, a polymer of repeating units of particular amino acid sequences, an antibody, an antibody fragment, an FcRn-binding material, an in vivo connective tissue, a nucleotide, fibronectin, transferrin, a saccharide, heparin, and elastin.

In still another specific embodiment, F is a polymer selected from the group consisting of polyethylene glycol, polypropylene glycol, an ethylene glycol-propylene glycol copolymer, polyoxyethylated polyol, polyvinyl alcohol, polysaccharide, dextran, polyvinyl ethyl ether, a biodegradable polymer, a lipid polymer, chitins, hyaluronic acid, an oligonucleotide, and a combination thereof.

In still another specific embodiment, F is an immunoglobulin Fc region.

In still another specific embodiment, F is an IgG Fc region.

In still another specific embodiment, L is selected from the group consisting of a peptide, fatty acid, a saccharide, a polymer, a low molecular weight compound, a nucleotide, and a combination thereof.

In still another specific embodiment, L is a polymer selected from the group consisting of polyethylene glycol, polypropylene glycol, an ethylene glycol-propylene glycol copolymer, polyoxyethylated polyol, polyvinyl alcohol, polysaccharide, dextran, polyvinyl ethyl ether, a biodegradable polymer, a lipid polymer, chitins, hyaluronic acid, an oligonucleotide, and a combination thereof.

In still another specific embodiment, L is polyethylene glycol.

Still another aspect of the present invention provides a polynucleotide encoding the conjugate, a vector including the polynucleotide, and a transformant including the polynucleotide or vector.

Still another aspect of the present invention provides a composition containing the conjugate.

In a specific embodiment, the composition is a pharmaceutical composition.

In another specific embodiment, the composition is for preventing or treating metabolic syndrome.

In still another specific embodiment, the metabolic syndrome may include impaired glucose tolerance, hypercholesterolemia, dyslipidemia, obesity, diabetes, hypertension, arteriosclerosis due to dyslipidemia, atherosclerosis, arteriosclerosis, or coronary heart disease.

Still another aspect of the present invention provides a method for treating a target disease, which includes administering the conjugate or a composition containing the conjugate to a subject in need thereof.

In a specific embodiment, the disease is metabolic syndrome.

Still another aspect of the present invention provides a use of the conjugate or composition containing the conjugate in the preparation of a medicament.

In a specific embodiment, the medicament is for preventing or treating metabolic syndrome.

Advantageous Effects of the Invention

The conjugate of the triple agonist according to the present invention has activities to a glucagon receptor, a glucagon-like peptide-1 (GLP-1) receptor, and a glucose-dependent insulinotropic polypeptide (GIP) receptor, and thus can be applied for the treatment of metabolic syndrome.

BRIEF DESCRIPTIONS OF THE DRAWINGS

FIG. 1 shows a histogram illustrating the measurement result of the body weight change in an obese animal model (mice) at two-day intervals, during the administration of a long-acting conjugate of a triple agonist via a high-fat diet to the mice once every two days for 28 days ($p<0.05$, $p<0.01$, *$p<0.001$, vs. vehicle by 1-way ANOVA).

FIG. 2 shows a histogram illustrating the measurement result of the amount of mesenteric fat in an obese animal model (mice) at two-day intervals, during the administration of a long-acting conjugate of a triple agonist via a high-fat diet to the mice once every two days for 28 days ($p<0.05$, $p<0.01$, *$p<0.001$, vs. vehicle by 1-way ANOVA).

DETAILED DESCRIPTION OF THE INVENTION

Hereinafter, the present invention will be described in more detail.

Meanwhile, each of the explanations and exemplary embodiments disclosed herein can be applied to other explanations and exemplary embodiments. That is, all of the combinations of various factors disclosed herein belong to the scope of the present invention. Furthermore, the scope of the present invention should not be limited by the specific disclosure provided hereinbelow.

Over the entire specification of the present invention, not only the conventional one-letter and three-letter codes for naturally occurring amino acids, but also those three-letter codes generally allowed for other amino acids, such as α-aminoisobutyric acid (Aib), Sar (N-methylglycine), and α-methyl-glutamic acid, are used.

Additionally, the amino acids mentioned herein are abbreviated according to the nomenclature rules of IUPAC-IUB as follows:

| | |
|---|---|
| alanine (Ala, A) | arginine (Arg, R) |
| asparagine (Asn, N) | aspartic acid (Asp, D) |
| cysteine (Cys, C) | glutamic acid (Glu, E) |
| glutamine (Gln, Q) | glycine (Gly, G) |

| histidine (His, H) | isoleucine (Ile, I) |
|---|---|
| leucine (Leu, L) | lysine (Lys, K) |
| methionine (Met, M) | phenylalanine (Phe, F) |
| proline (Pro, P) | serine (Ser, S) |
| threonine (Thr, T) | tryptophan (Trp, W) |
| tyrosine (Tyr, Y) | valine (Val, V) |

An aspect of the present invention provides a conjugate of a peptide which has activities to a glucagon receptor, a glucagon-like peptide-1 (GLP-1) receptor, and a glucose-dependent insulinotropic polypeptide (GIP) receptor.

In the present invention, the conjugate of a peptide, which has activities to a glucagon receptor, a GLP-1 receptor, and a GIP receptor, may be in a form in which a biocompatible material is conjugated to the peptide for increasing the in vivo half-life of the peptide. In the present invention, the biocompatible material can be used interchangeably with a carrier.

In the present invention, the conjugate of the peptide can exhibit increased duration of efficacy compared to the peptide, to which the carrier is not conjugated, and the conjugate is called herein as "long-acting conjugate".

Meanwhile, such conjugate may be non-naturally occurring.

In a specific embodiment of the present invention, the conjugate is a conjugate represented by Chemical Formula 1 below:

X-La-F      [Chemical Formula 1]

wherein,

X is a peptide having activities to a glucagon receptor, a glucagon-like peptide-1 (GLP-1) receptor, and a glucose-dependent insulinotropic polypeptide (GIP) receptor;

L is a linker;

a is 0 or a positive integer, with the proviso that when a is 2 or greater, each L is independent from each other; and F is a material capable of increasing the half-life of X.

In the present invention, the "peptide having activities to a glucagon receptor, a GLP-1 receptor, and a GIP receptor" may correspond to a constitution of one moiety that constitutes the above conjugate. Specifically, the peptide corresponds to X in Chemical Formula 1 above.

In the present invention, the peptide having activities to the glucagon receptor, GLP-1 receptor, and GIP receptor can be used interchangeably with a triple agonist.

The peptide may include various materials (e.g., various peptides) which have a significant level of activities to glucagon, GLP-1, and GIP receptors.

The triple agonist having a significant level of activities to glucagon, GLP-1, and GIP receptors may exhibit in vitro activities of 0.1% or higher, 1% or higher, 2% or higher, 3% or higher, 4% or higher, 5% or higher, 6% or higher, 7% or higher, 8% or higher, 9% or higher, 10% or higher, 20% or higher, 30% or higher, 40% or higher, 50% or higher, 60% or higher, 70% or higher, 80% or higher, 90% or higher, and 100% or higher, to one or more receptors, specifically two or more receptors, and more specifically all three of the receptors among the glucagon, GLP-1, and GIP receptors, compared to native ligands of the corresponding receptors (native glucagon, native GLP-1, and native GIP), but is not particularly limited thereto.

The method for measuring the in vitro activities of the triple agonist may refer to Experimental Example 1 of the present invention, but is not particularly limited thereto.

Meanwhile, the triple agonist is characterized by having one or more, two or more, and specifically all three of the following activities of i) to iii), specifically a significant activity(-ies) thereof:

i) activation of a GLP-1 receptor; ii) activation of a glucagon receptor; and iii) activation of a GIP receptor.

In particular, the activation of receptors may include, for example, those cases where the in vitro activities of the peptide are 0.1% or higher, 1% or higher, 2% or higher, 3% or higher, 4% or higher, 5% or higher, 6% or higher, 7% or higher, 8% or higher, 9% or higher, 10% or higher, 20% or higher, 30% or higher, 40% or higher, 50% or higher, 60% or higher, 70% or higher, 80% or higher, 90% or higher, and 100% or higher, compared to native ligands of the corresponding receptors, but the activation is not limited thereto.

Additionally, the triple agonist may be one which has an increased in vivo half-life relative to any one of native GLP-1, native glucagon, and native GIP, but is not particularly limited thereto.

The above glucagon analog may be one which is non-naturally occurring, but is not particularly limited thereto.

Specifically, the isolated peptide may be an analog of native glucagon, but is not particularly limited thereto.

The native glucagon analog according to the present invention may include peptides which have at least one difference in amino acid sequence compared to that of native glucagon; peptides which were modified via modification of the native glucagon sequence; and mimetics of the native glucagon.

Meanwhile, native glucagon may have the following amino acid sequence, but is not particularly limited thereto:

```
                                    (SEQ ID NO: 118)
His-Ser-Gln-Gly-Thr-Phe-Thr-Ser-Asp-Tyr-Ser-Lys-

Tyr-Leu-Asp-Ser-Arg-Arg-Ala-Gln-Asp-Phe-Val-Gln-

Trp-Leu-Met-Asn-Thr
```

Specifically, the isolated peptide may be an analog of native glucagon with a variation selected from the group consisting of substitution, addition, deletion, modification, and a combination thereof, on at least one amino acid of the native glucagon sequence, but is not particularly limited thereto.

Additionally, the substitution of the amino acid may include both a substitution to an amino acid and a substitution to a non-native compound.

Additionally, the addition may be performed at the N-terminus and/or C-terminus of a peptide. Meanwhile, the length of the amino acid for addition is not particularly limited, but 1 or more, 2 or more, 3 or more, 4 or more, 5 or more, 6 or more, 7 or more, 8 or more, 9 or more, 10 or more, and 11 or more amino acids may be added, and in a broad sense, the addition may include the addition of a polypeptide, but is not particularly limited thereto.

More specifically, the glucagon analog may be those where 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 amino acids selected from the group consisting of amino acids at positions 1, 2, 3, 7, 10, 12, 13, 14, 15, 16, 17, 18, 19, 20, 21, 23, 24, 27, 28, and 29 in the amino acid sequence of native glucagon are substituted with other amino acids, and in addition, may be those where 1 or more, 2 or more, 3 or more, 4 or more, 5 or more, 6 or more, 7 or more, 8 or more, 9 or more, 10 or more, or 11 or more amino acids are independently or additionally added to the C-terminus thereof, but is not particularly limited thereto.

Even more specifically, the glucagon analog may be those where 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, or 19 amino acids selected from the group consisting of amino acids at positions 1, 2, 3, 10, 12, 13, 14, 15, 16, 17, 18, 19, 20, 21, 23, 24, 27, 28, and 29 in the amino acid sequence of native glucagon are substituted with other amino acids, and in addition, may be those where 1 or more, 2 or more, 3 or more, 4 or more, 5 or more, 6 or more, 7 or more, 8 or more, 9 or more, 10 or more, or 11 or more amino acids are independently or additionally added to the C-terminus thereof, but is not particularly limited thereto.

Even more specifically, the glucagon analog may be those where 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, or 17 amino acids selected from the group consisting of amino acids at positions 1, 2, 3, 10, 13, 14, 15, 16, 17, 18, 19, 20, 21, 23, 24, 28, and 29 in the amino acid sequence of native glucagon are substituted with other amino acids, and in addition, may be those where 1 or more, 2 or more, 3 or more, 4 or more, 5 or more, 6 or more, 7 or more, 8 or more, 9 or more, 10 or more, or 11 or more amino acids are independently or additionally added to the C-terminus thereof, but is not particularly limited thereto.

Even more specifically, the glucagon analog may be those where 1 or more, 2 or more, 3 or more, 4 or more, 5 or more, 6 or more, 7 or more, 8 or more, 9 or more, 10 or more, 11 or more, 12 or more, 13 or more, or 14 amino acids selected from the group consisting of amino acids at positions 1, 2, 13, 16, 17, 18, 19, 20, 21, 23, 24, 27, 28, and 29 in the amino acid sequence of native glucagon are substituted with other amino acids, and in addition, may be those where 1 or more, 2 or more, 3 or more, 4 or more, 5 or more, 6 or more, 7 or more, 8 or more, 9 or more, 10 or more, or 11 or more amino acids are independently or additionally added to the C-terminus thereof, but is not particularly limited thereto.

The amino acids to be introduced into the above native glucagon may be selected from the group consisting of tyrosine, α-methyl-glutamic acid, Aib, methionine, glutamic acid, histidine, lysine, leucine, isoleucine, glutamine, valine, glycine, alanine, cysteine, serine, alanine, aspartic acid, and arginine, but are not particularly limited thereto.

For example, the amino acid sequence(s) to be added may be at least one amino acid sequence derived from a native GLP-1, native GIP, or native exendin-4 amino acid sequence.

The glucagon analog or triple agonist may include an intramolecular bridge (e.g., a covalent crosslinking or non-covalent crosslinking), and specifically, is in a form including a ring, for example, is in a form where a ring is formed between the $16^{th}$ amino acid and the $20^{th}$ amino acid of the glucagon analog or the triple agonist, but is not particularly limited thereto.

The non-limiting example of the ring may include a lactam bridge (or a lactam ring).

Additionally, the glucagon analog or triple agonist includes all of those which are modified to include a ring, or include an amino acid capable of forming a ring in a target position.

For example, the glucagon analog or triple agonist may be one where the amino acid pair of the $16^{th}$ and $20^{th}$ amino acids are substituted with glutamic acid or lysine, which can form a ring, respectively, but the glucagon analog or triple agonist are not limited thereto.

The ring may be formed between amino acid side chains within the glucagon analog or triple agonist; for example, they may be in the form of a lactam ring between a side chain of lysine and a side chain of glutamic acid, but the ring is not particularly limited thereto.

Examples of the glucagon analog prepared by a combination of these methods may include peptides, whose amino acid sequences differ from that of native glucagon in at least one amino acid, and in which the α-carbon in the N-terminus thereof is removed, while having activities to a glucagon receptor, a GLP-1 receptor, and a GIP receptor, etc., but are not limited thereto, and analogs of native glucagon applicable to the present invention can be prepared by combining various methods for the preparation of analogs.

Additionally, with respect to the triple agonist of the present invention, a part of the amino acids may be substituted with other amino acids or non-natural compounds to avoid the recognition by peptidase for increasing the in vivo half life of the triple agonist, but the triple agonist is not particularly limited thereto.

Specifically, the peptide may be a peptide where the in vivo half life was increased by avoiding the recognition by the peptidase via substitution of the $2^{nd}$ amino acid sequence among the amino acid sequences of the triple agonist, but any substitution or modification of amino acids to avoid the recognition by in vivo peptidase is included without limitation.

Additionally, such modification for preparing analogs of native glucagon may include all of the modifications using L-type or D-type amino acids and/or non-natural amino acids; and/or a modification of native sequence, for example, a modification of a side chain functional group, an intramolecular covalent bonding (e.g., a ring formation between side chains), methylation, acylation, ubiquitination, phosphorylation, aminohexanation, biotinylation, etc.

Additionally, the modification may also include all of those where one or more amino acids are added to the amino and/or carboxy terminus of native glucagon.

During the substitution or addition of amino acids, not only the 20 amino acids commonly found in human proteins, but also atypical or non-naturally occurring amino acids may be used. Commercial sources of atypical amino acids may include Sigma-Aldrich, ChemPep Inc., and Genzyme Pharmaceuticals. The peptides including these amino acids and typical peptide sequences may be synthesized and purchased from commercial suppliers, e.g., American Peptide Company, Bachem (USA), or Anygen (Korea).

Amino acid derivatives may be obtained in the same manner, and as one such example, 4-imidazoacetic acid may be used.

Additionally, the peptide according to the present invention may be in the form of a variant where the amino and/or carboxy terminus, etc. of the peptide is chemically modified or protected by organic groups, or amino acids may be added to the terminus of the peptide, for its protection from proteases in vivo while increasing its stability.

In particular, in the case of a chemically-synthesized peptide, its N- and C-termini are electrically charged and thus the N- and C-termini of the peptide may be acetylated and/or amidated, but the peptide is not particularly limited thereto.

Additionally, the peptide according to the present invention may include all of those in the form of the peptide itself, a salt thereof (e.g., a pharmaceutically acceptable salt thereof), or a solvate thereof. Additionally, the peptide may be in any pharmaceutically acceptable form.

The kind of the salt is not particularly limited. However, the salt is preferably one that is safe and effective to a subject, e.g., a mammal, but is not particularly limited thereto.

The term "pharmaceutically acceptable" refers to a material which can be effectively used for the intended use within the scope of pharmaco-medical decision without inducing excessive toxicity, irritation, allergic responses, etc.

As used herein, the term "pharmaceutically acceptable salt" refers to a salt derived from pharmaceutically acceptable inorganic acids, organic acids, or bases. Examples of the suitable salts may include hydrochloric acid, bromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, citric acid, methanesulfonic acid, formic acid, benzoic acid, malonic acid, naphthalene-2-sulfonic acid, benzenesulfonic acid, etc. Examples of the salts derived from suitable bases may include alkali metals such as sodium, potassium, etc.; alkali earth metals such as magnesium; ammonium, etc.

As used herein, the term "solvate" refers to a complex formed between the peptide according to the present invention or a salt thereof and a solvent molecule.

In a specific embodiment, X may be a peptide which includes an amino acid sequence represented by General Formula 1 below.

(General Formula 1, SEQ ID NO: 103)
Xaa1-Xaa2-Xaa3-Gly-Thr-Phe-Xaa7-Ser-Asp-Xaa10-Ser- Xaa12-Xaa13-Xaa14-Xaa15-Xaa16-Xaa17-Xaa18-Xaa19-

Xaa20-Xaa21-Phe-Xaa23-Xaa24-Trp-Leu-Xaa27-Xaa28-

Xaa29-Xaa30-R1

In General Formula 1 above,

Xaa1 is histidine (His, H), 4-imidazoacetyl (CA), or tyrosine (Tyr, Y);

Xaa2 is glycine (Gly, G), a-methyl-glutamic acid, or Aib;

Xaa3 is glutamic acid (Glu, E) or glutamine (Gln, Q);

Xaa7 is threonine (Thr, T) or isoleucine (Ile, I);

Xaa10 is leucine (Leu, L), tyrosine (Tyr, Y), lysine (Lys, K), cysteine (Cys, C), or valine (Val, V);

Xaa12 is lysine (Lys, K), serine (Ser, S), or isoleucine (Ile, I);

Xaa13 is glutamine (Gln, Q), tyrosine (Tyr, Y), alanine (Ala, A), or cysteine (Cys, C);

Xaa14 is leucine (Leu, L), methionine (Met, M), or tyrosine (Tyr, Y);

Xaa15 is cysteine (Cys, C), aspartic acid (Asp, D), glutamic acid (Glu, E), or leucine (Leu, L);

Xaa16 is glycine (Gly, G), glutamic acid (Glu, E), or serine (Ser, S);

Xaa17 is glutamine (Gln, Q), arginine (Arg, R), isoleucine (Ile, I), glutamic acid (Glu, E), cysteine (Cys, C), or lysine (Lys, K);

Xaa18 is alanine (Ala, A), glutamine (Gln, Q), arginine (Arg, R), or histidine (His, H);

Xaa19 is alanine (Ala, A), glutamine (Gln, Q), cysteine (Cys, C), or valine (Val, V);

Xaa20 is lysine (Lys, K), glutamine (Gln, Q), or arginine (Arg, R);

Xaa21 is glutamic acid (Glu, E), glutamine (Gln, Q), leucine (Leu, L), cysteine (Cys, C), or aspartic acid (Asp, D);

Xaa23 is isoleucine (Ile, I) or valine (Val, V);

Xaa24 is alanine (Ala, A), glutamine (Gln, Q), cysteine (Cys, C), asparagine (Asn, N), aspartic acid (Asp, D), or glutamic acid (Glu, E);

Xaa27 is valine (Val, V), leucine (Leu, L), lysine (Lys, K), or methionine (Met, M);

Xaa28 is cysteine (Cys, C), lysine (Lys, K), alanine (Ala, A), asparagine (Asn, N), or aspartic acid (Asp, D);

Xaa29 is cysteine (Cys, C), glycine (Gly, G), glutamine (Gln, Q), threonine (Thr, T), glutamic acid (Glu, E), or histidine (His, H);

Xaa30 is cysteine (Cys, C), glycine (Gly, G), lysine (Lys, K), or histidine (His, H), or is absent;

R1 is cysteine (Cys, C), GKKNDWKHNIT (SEQ ID NO: 106), m-SSGAPPPS-n (SEQ ID NO: 107), or m-SSGQP-PPS-n (SEQ ID NO: 108), or is absent;

wherein, m is -Cys-, -Pro-, or -Gly-Pro-;

n is -Cys-, -Gly-, -Ser-, or -His-Gly-, or is absent.

For example, the triple agonist may be one which includes an amino acid sequence selected from the group consisting of SEQ ID NOS: 1 to 102; and one which (essentially) consists of an amino acid sequence selected from the group consisting of SEQ ID NOS: 1 to 102, but is not limited thereto.

Additionally, although described as "a peptide consisting of a particular SEQ ID NO" in the present invention, it does not exclude a mutation that may occur by the addition of a meaningless sequence upstream or downstream of the amino acid sequence of the corresponding SEQ ID NO, or a mutation that may occur naturally, or a silent mutation thereof, as long as the peptide has an activity the same as or corresponding to that of the peptide which consists of an amino acid sequence of the corresponding SEQ ID NO, and even when the sequence addition or mutation is present, it obviously belongs to the scope of the present invention.

The above may be applicable in other specific embodiments or aspects of the present invention, but is not limited thereto.

Specifically, in General Formula 1 above, Xaa14 may be leucine or methionine, and Xaa15 may be cysteine, aspartic acid, or leucine.

Examples of the peptide may include a peptide which includes an amino acid sequence selected from the group consisting of SEQ ID NOS: 1 to 12, 14 to 17, and 21 to 102 or a peptide which (essentially) consists of the same, but are not particularly limited thereto.

The peptide may significantly activate at least one of the glucagon receptor, GLP-1 receptor, and GIP receptor, but is not particularly limited thereto. Specifically, the peptide may be one which significantly activates the GLP-1 receptor, or additionally the glucagon receptor and/or GIP receptor, but is not particularly limited thereto.

Even more specifically, the peptide may be:

in General Formula 1 above,

Xaa2 is glycine, α-methyl-glutamic acid, or Aib;

Xaa7 is threonine;

Xaa10 is tyrosine, cysteine, or valine;

Xaa12 is lysine or isoleucine;

Xaa13 is tyrosine, alanine, glutamine, or cysteine;

Xaa14 is leucine, cysteine, or methionine;

Xaa15 is cysteine, leucine, glutamic acid, or aspartic acid;

Xaa17 is glutamine, arginine, isoleucine, cysteine, glutamic acid, or lysine;

Xaa18 is alanine, glutamine, arginine, or histidine;
Xaa19 is alanine, glutamine, valine, or cysteine;
Xaa20 is lysine, arginine, or glutamine;
Xaa21 is glutamic acid, glutamine, leucine, cysteine, or aspartic acid;
Xaa23 is isoleucine or valine;
Xaa24 is cysteine, alanine, glutamine, asparagine, glutamic acid, or aspartic acid; and
Xaa27 is leucine or lysine, but is not particularly limited thereto.

Even more specifically,
in General Formula 1 above,
Xaa2 is glycine, α-methyl-glutamic acid, or Aib;
Xaa7 is threonine;
Xaa10 is tyrosine, cysteine, or valine;
Xaa12 is lysine or isoleucine;
Xaa13 is tyrosine, alanine, or cysteine;
Xaa14 is leucine or methionine;
Xaa15 is cysteine or aspartic acid;
Xaa17 is glutamine, arginine, isoleucine, cysteine, or lysine;
Xaa18 is alanine, arginine, or histidine;
Xaa19 is alanine, glutamine, or cysteine;
Xaa20 is lysine or glutamine;
Xaa21 is glutamic acid, cysteine, or aspartic acid;
Xaa23 is valine;
Xaa24 is alanine, glutamine, cysteine, asparagine, or aspartic acid; and
Xaa27 is leucine or lysine, but is not particularly limited thereto.

Even more specifically,
in General Formula 1 above,
Xaa2 is α-methyl-glutamic acid or Aib;
Xaa7 is threonine;
Xaa10 is tyrosine or cysteine;
Xaa12 is lysine or isoleucine;
Xaa13 is tyrosine, alanine, or cysteine;
Xaa14 is leucine or methionine;
Xaa15 is cysteine or aspartic acid;
Xaa16 is glutamic acid;
Xaa17 is arginine, isoleucine, cysteine, or lysine;
Xaa18 is alanine, arginine, or histidine;
Xaa19 is alanine, glutamine, or cysteine;
Xaa20 is lysine or glutamine;
Xaa21 is glutamic acid or aspartic acid;
Xaa23 is valine;
Xaa24 is glutamine, asparagine, or aspartic acid;
Xaa27 is leucine; and
Xaa28 is cysteine, alanine, asparagine, or aspartic acid.

Specifically,
in General Formula 1 above,
Xaa1 is histidine or 4-imidazoacetyl;
Xaa2 is α-methyl-glutamic acid or Aib;
Xaa3 is glutamine;
Xaa7 is threonine;
Xaa10 is tyrosine;
Xaa12 is isoleucine;
Xaa13 is alanine or cysteine;
Xaa14 is methionine;
Xaa15 is aspartic acid;
Xaa16 is glutamic acid;
Xaa17 is isoleucine or lysine;
Xaa18 is alanine or histidine;
Xaa19 is glutamine or cysteine;
Xaa20 is lysine;
Xaa21 is aspartic acid;
Xaa23 is valine;
Xaa24 is asparagine;
Xaa27 is leucine;
Xaa28 is alanine or asparagine;
Xaa29 is glutamine or threonine; and
Xaa30 is cysteine or lysine, or is absent.

More specifically,
in General Formula 1 above,
Xaa2 is glycine, α-methyl-glutamic acid, or Aib;
Xaa3 is glutamine;
Xaa7 is threonine;
Xaa10 is tyrosine, cysteine, or valine;
Xaa12 is lysine;
Xaa13 is tyrosine;
Xaa14 is leucine;
Xaa15 is aspartic acid;
Xaa16 is glycine, glutamic acid, or serine;
Xaa17 is glutamine, arginine, cysteine, or lysine;
Xaa18 is alanine, arginine, or histidine;
Xaa19 is alanine or glutamine;
Xaa20 is lysine or glutamine;
Xaa21 is glutamic acid, cysteine, or aspartic acid;
Xaa23 is valine;
Xaa24 is alanine, glutamine, or cysteine;
Xaa27 is leucine or lysine; and
Xaa29 is glycine, glutamine, threonine, or histidine;
but is not particularly limited thereto.

These peptides may correspond to a case where the peptide has significant activation levels on both the GLP-1 receptor and glucagon receptor, or higher activation levels compared to that on the GIP receptor; a case where the peptide has significant activation levels on all of the GLP-1 receptor, glucagon receptor, and GIP receptor; or a case where the peptide has significant activation levels on both the GLP-1 receptor and GIP receptor and higher activation levels compared to that on the glucagon receptor; but are not particularly limited thereto.

When the peptide has significant activation levels on both the GLP-1 receptor and GIP receptor, and also higher activation levels compared to that on the glucagon receptor, it is possible to provide a peptide with more improved capability of controlling blood glucose levels along with the effect of reducing body weight, whereas when the peptide has significant activation levels on all of the GLP-1 receptor, glucagon receptor, and GIP receptor, there is an advantage in that the effect of reducing body weight can be maximized, but the effects are not particularly limited thereto.

Examples of the peptide may include a peptide which includes an amino acid sequence selected from the group consisting of SEQ ID NOS: 8, 9, 21 to 37, 39, 42, 43, 49 to 61, 64 to 83, 85, 86, 88, 89, 91 to 93, and 95 to 102; or a peptide which (essentially) consists of the same, but are not particularly limited thereto.

In a specific embodiment, the peptide may include an amino acid sequence represented by General Formula 2 below.

```
                    (General Formula 2, SEQ ID NO: 104)
Xaa1-Xaa2-Gln-Gly-Thr-Phe-Thr-Ser-Asp-Xaa10-Ser- Lys-Xaa13-Xaa14-Xaa15-Xaa16-Xaa17-Xaa18-Xaa19-

Xaa20-Xaa21-Phe-Xaa23-Xaa24-Trp-Leu-Leu-Xaa28-

Xaa29-Xaa30-Xaa31-Ser-Ser-Gly-Gln-Pro-Pro-Pro-

Ser-Xaa40
```

In General Formula 2 above,
Xaa1 is 4-imidazoacetyl, histidine, or tyrosine;
Xaa2 is glycine, α-methyl-glutamic acid, or Aib;
Xaa10 is tyrosine or cysteine;
Xaa13 is alanine, glutamine, tyrosine, or cysteine;
Xaa14 is leucine, methionine, or tyrosine;
Xaa15 is aspartic acid, glutamic acid, or leucine;
Xaa16 is glycine, glutamic acid, or serine;
Xaa17 is glutamine, arginine, isoleucine, glutamic acid, cysteine, or lysine;
Xaa18 is alanine, glutamine, arginine, or histidine;
Xaa19 is alanine, glutamine, cysteine, or valine;
Xaa20 is lysine, glutamine, or arginine;
Xaa21 is cysteine, glutamic acid, glutamine, leucine, or aspartic acid;
Xaa23 is isoleucine or valine;
Xaa24 is cysteine, alanine, glutamine, asparagine, or glutamic acid;
Xaa28 is lysine, cysteine, asparagine, or aspartic acid;
Xaa29 is glycine, glutamine, cysteine, or histidine;
Xaa30 is cysteine, glycine, lysine, or histidine;
Xaa31 is proline or cysteine; and
Xaa40 is cysteine or is absent.
More specifically, in General Formula 2 above,
Xaa13 is alanine, tyrosine, or cysteine;
Xaa15 is aspartic acid or glutamic acid;
Xaa17 is glutamine, arginine, cysteine, or lysine;
Xaa18 is alanine, arginine, or histidine;
Xaa21 is cysteine, glutamic acid, glutamine, or aspartic acid;
Xaa23 is isoleucine or valine;
Xaa24 is cysteine, glutamine, or asparagine;
Xaa28 is cysteine, asparagine, or aspartic acid;
Xaa29 is glutamine, cysteine, or histidine; and
Xaa30 is cysteine, lysine, or histidine.

Examples of the peptide may include a peptide which includes an amino acid sequence selected from the group consisting of SEQ ID NOS: 21, 22, 42, 43, 50, 64 to 77, and 95 to 102; more specifically, a peptide which includes an amino acid sequence selected from the group consisting of SEQ ID NOS: 21, 22, 42, 43, 50, 64 to 77, and 96 to 102; or a peptide which (essentially) consists of the same, but are not particularly limited thereto.

In a specific embodiment, the peptide may include an amino acid sequence represented by General Formula 3 below.

(General Formula 3, SEQ ID NO: 105)
Xaa1-Xaa2-Gln-Gly-Thr-Phe-Thr-Ser-Asp-Tyr-Ser-Lys- Xaa13-Leu-Asp-Glu-Xaa17-Xaa18-Xaa19-Lys-Xaa21-Phe- Val-Xaa24-Trp-Leu-Leu-Xaa28-Xaa29-Xaa30-Xaa31-Ser- Ser-Gly-Gln-Pro-Pro-Pro-Ser-Xaa40

In General Formula 3 above,
Xaa1 is histidine or tyrosine;
Xaa2 is α-methyl-glutamic acid or Aib;
Xaa13 is alanine, tyrosine or cysteine;
Xaa17 is arginine, cysteine, or lysine;
Xaa18 is alanine or arginine;
Xaa19 is alanine or cysteine;
Xaa21 is glutamic acid or aspartic acid;
Xaa24 is glutamine or asparagine,
Xaa28 is cysteine or aspartic acid;
Xaa29 is cysteine, histidine, or glutamine;
Xaa30 is cysteine or histidine;
Xaa31 is proline or cysteine; and
Xaa40 is cysteine or is absent.

Examples of the peptide may include a peptide which includes an amino acid sequence selected from the group consisting of SEQ ID NOS: 21, 22, 42, 43, 50, 64 to 71, 75 to 77, and 96 to 102; or a peptide which (essentially) consists of the same, but are not particularly limited thereto.

Additionally, in General Formula 1 above, R1 may be cysteine, GKKNDWKHNIT (SEQ ID NO: 106), CSSGQP-PPS (SEQ ID NO: 109), GPSSGAPPPS (SEQ ID NO: 110), GPSSGAPPPSC (SEQ ID NO: 111), PSSGAPPPS (SEQ ID NO: 112), PSSGAPPPSG (SEQ ID NO: 113), PSSGAPPP-SHG (SEQ ID NO: 114), PSSGAPPPSS (SEQ ID NO: 115), PSSGQPPPS (SEQ ID NO: 116), or PSSGQPPPSC (SEQ ID NO: 117), or is absent, but is not particularly limited thereto.

Additionally, the peptide of the present invention may be synthesized by a method well-known in the art, according to its length, e.g., by an automatic peptide synthesizer, and may be produced by genetic engineering technology.

Specifically, the peptide of the present invention may be prepared by a standard synthesis method, a recombinant expression system, or any other method known in the art. Accordingly, the peptide of the present invention may be synthesized by many methods including, for example, the methods described below:

(a) a method of synthesizing a peptide by a solid-phase or liquid-phase method stepwise or by fragment assembly, followed by isolation and purification of the final peptide product; or (b) a method of expressing a nucleic acid construct encoding a peptide in a host cell and recovering the expression product from the host cell culture; or (c) a method of performing an in vitro cell-free expression of a nucleic acid construct encoding a peptide and recovering the expression product therefrom; or a method of obtaining peptide fragments by any combination of the methods (a), (b), and (c), obtaining the peptide by linking the peptide fragments, and then recovering the peptide.

In the above conjugate, F is a material which can increase the half-life of X, i.e., a peptide having activities to a glucagon receptor, GLP-1 receptor, and GIP receptor, and it corresponds to a constitution of a moiety constituting the conjugate of the present invention.

The F and the X may be bound to each other via a covalent chemical bond or non-covalent chemical bond; or F and X may be bound to each other through L via a covalent chemical bond, a non-covalent chemical bond, or a combination thereof.

The material which can increase the half-life of X may be a biocompatible material, for example, one selected from the group consisting of a polymer, fatty acid, cholesterol, albumin and a fragment thereof, an albumin-binding material, a polymer of repeating units of particular amino acid sequences, an antibody, an antibody fragment, an FcRn-binding material, an in vivo connective tissue, a nucleotide, fibronectin, transferrin, a saccharide, heparin, and elastin, but is not particularly limited thereto.

The elastin may be human tropoelastin, which is a water-soluble precursor, and may be a certain sequence of tropoelastin or a polymer of certain repeating units of them, for example, inclusive of all elastin-analogous polypeptides, but is not particularly limited thereto.

Examples of the polymer may be one selected from the group consisting of polyethylene glycol (PEG), polypropylene glycol, an ethylene glycol-propylene glycol copolymer, polyoxyethylated polyol, polyvinyl alcohol, polysaccharide, dextran, polyvinyl ethyl ether, a biodegradable polymer, a lipid polymer, chitins, hyaluronic acid, an oligonucleotide, and a combination thereof, but are not particularly limited thereto.

The polyethylene glycol encompasses all of the forms of homopolymers of ethylene glycol, PEG copolymers, and monomethyl-substituted PEG polymers (mPEG), but is not particularly limited thereto.

Additionally, the biocompatible material may include poly-amino acids such as poly-lysine, poly-aspartic acid, and poly-glutamic acid, but is not limited thereto.

Additionally, the fatty acid may be one having a binding affinity to albumin in vivo, but is not particularly limited thereto.

In a more specific embodiment, the FcRn-binding material may be an immunoglobulin Fc region, and more specifically, an IgG Fc region, but is not particularly limited thereto.

The at least one amino acid side chain within the peptide of the present invention may be attached to the biocompatible material in order to increase solubility and/or half-life in vivo, and/or increase bioavailability thereof. These modifications can reduce the clearance of therapeutic proteins and peptides.

The biocompatible polymer may be water-soluble (amphipathic or hydrophilic) and/or non-toxic and/or pharmaceutically acceptable.

F may be directly linked to X (i.e., a is 0 in Chemical Formula 1) or may be linked via a linker (L).

Specifically, L may be a peptide linker or a non-peptide linker, but is not limited thereto.

When L is a peptide linker, it can include one or more amino acids, for example, 1 to 1000 amino acids, but is not particularly limited thereto. In the present invention, various known peptide linkers may be used to link between F and X (e.g., including [GS]x linker, [GGGS]x linker, and [GGGGS]x linker, etc., wherein x is a natural number of at least 1), but the peptide linkers are not limited thereto.

In the present invention, the "non-peptide linker" includes a biocompatible polymer to which at least two repeating units are linked. The repeating units are linked with each other by any covalent bond instead of a peptide bond. The non-peptide linker may be one constitution that establishes a moiety of the conjugate of the present invention and correspond to L in Chemical Formula 1 above.

In La of Chemical Formula 1, a may be 1 or greater, and each L may be independent from each other when a is 2 or greater.

As used herein, the term "non-peptide linker" may be used interchangeably with "non-peptide polymer".

Additionally, in a specific embodiment, the conjugate may be one in which F and X are covalently linked to each other by a non-peptide linker having two reactive end groups which are linked to X, specifically peptide drug, and F, specifically immunoglobulin Fc region, respectively.

Specifically, the non-peptide linker may be one selected from the group consisting of fatty acid, a saccharide, a polymer, a low molecular weight compound, a nucleotide, and a combination thereof.

Although not particularly limited, the non-peptide linker may be one selected from the group consisting of polyethylene glycol, polypropylene glycol, an ethylene glycol-propylene glycol copolymer, polyoxyethylated polyol, polyvinyl alcohol, a polysaccharide, dextran, polyvinyl ethyl ether, a biodegradable polymer such as polylactic acid (PLA) and polylactic-glycolic acid (PLGA), lipid polymer, chitins, hyaluronic acid, an oligonucleotide, and a combination thereof. In a more specific embodiment, the non-peptide polymer may be polyethylene glycol, but is not limited thereto. Additionally, the derivatives of the above materials already known in the art and the derivatives that can be easily produced at the technology level in the art belong to the scope of the present invention.

The non-peptide linker to be used in the present invention may be any polymer which has a resistance to proteases in vivo, without limitation. The molecular weight of the non-peptide polymer may be in the range of 1 kDa to 100 kDa, and specifically, 1 kDa to 20 kDa, but is not limited thereto. Additionally, the non-peptide linker of the present invention, which is linked to the polypeptide corresponding to F may include not only a single kind of a polymer but also a combination of different kinds of polymers.

In a specific embodiment, both ends of the non-peptide linker may be respectively linked to an amine group or thiol group of F, for example an immunoglobulin Fc region, or an amine group or thiol group of X.

Specifically, the non-peptide polymer may include a reactive group which can be linked to F (e.g., an immunoglobulin Fc region) and X at both ends thereof, respectively, and specifically, a reactive group which can be linked to an amine group located at the N-terminus or lysine, or a thiol group of cysteine of X, or an amine group located at the N-terminus or lysine, or a thiol group of cysteine of F (e.g., an immunoglobulin Fc region), but the reactive group is not limited thereto.

Additionally, the reactive group of the non-peptide polymer that can be linked to the immunoglobulin Fc region and X may be selected from the group consisting of an aldehyde group, a maleimide group, and a succinimide derivative, but is not limited thereto.

In the above, examples of the aldehyde group may include a propionaldehyde group or a butyraldehyde group, but are not limited thereto.

In the above, as a succinimide derivative, succinimidyl valerate, succinimidyl methylbutanoate, succinimidyl methylpropionate, succinimidyl butanoate, succinimidyl propionate, N-hydroxysuccinimide, hydroxy succinimidyl, succinimidyl carboxymethyl, or succinimidyl carbonate may be used, but the succinimide derivative is not limited thereto.

The non-peptide linker may be linked to X and F via these reactive groups, but the reactive groups are not particularly limited thereto.

Additionally, the final product produced through reductive alkylation via an aldehyde bond is more stable than that linked by an amide bond. The aldehyde reactive group selectively reacts with a N-terminus at a low pH condition while it can form a covalent bond with a lysine residue at high pH (e.g., pH 9.0).

The reactive groups at both ends of the non-peptide linker may be the same as or different from each other, for example, a maleimide reactive group may be provided at one end, whereas an aldehyde group, a propionaldehyde group, or a butyraldehyde group may be provided at the other end. However, as long as F, specifically an immunoglobulin Fc region, can be linked to X, and the reactive groups are not particularly limited.

For example, the non-peptide linker may have a maleimide group as a reactive group at one end while having an aldehyde group, a propionaldehyde group, or a butyraldehyde group, etc., at the other end.

When a polyethylene glycol having a reactive hydroxy group at both ends thereof is used as the non-peptide polymer, the hydroxy group may be activated to various reactive groups by known chemical reactions, or a polyethylene glycol having a commercially-available modified reactive group may be used so as to prepare the long-acting protein conjugate of the present invention.

In a specific embodiment, the non-peptide polymer may be one which can be linked to a cysteine residue of X, and more specifically, to the —SH group of cysteine, but is not limited thereto.

When maleimide-PEG-aldehyde is used, the maleimide group may be linked to the —SH group of X by a thioether bond, and the aldehyde group may be linked to F, specifically to the —NH$_2$ of the immunoglobulin Fc through reductive alkylation, but is not limited thereto, and the above is merely an embodiment.

Additionally, in the above conjugate, a reactive group of the non-peptide polymer may be linked to the —NH$_2$ located at the N-terminus of the immunoglobulin Fc, but this is merely an embodiment.

In the present invention, "immunoglobulin Fc region" refers to a region including the heavy chain constant region 2 (CH2) and/or the heavy chain constant region 3 (CH3), excluding the heavy chain and light chain variable regions of an immunoglobulin. The immunoglobulin Fc region may be one constitution that establishes a moiety of a protein conjugate of the present invention.

The immunoglobulin Fc region may include a hinge region in the heavy chain constant region, but is not limited thereto. Additionally, the immunoglobulin Fc region of the present invention may be an extended Fc region including a part or the entirety of the heavy chain constant region 1 (CH1) and/or the light chain constant region 1 (CL1), excluding the heavy chain and the light chain variable regions of the immunoglobulin, as long as the immunoglobulin Fc region has an effect substantially the same as or improved compared to the native type. Additionally, the immunoglobulin Fc region of the present invention may be a region in which a fairly long part of the amino acid sequence corresponding to CH2 and/or CH3 is removed.

For example, the immunoglobulin Fc region of the present invention may be 1) a CH1 domain, a CH2 domain, a CH3 domain, and a CH4 domain; 2) a CH1 domain and a CH2 domain; 3) a CH1 domain and a CH3 domain; 4) a CH2 domain and a CH3 domain; 5) a combination between one or two or more domains among a CH1 domain, a CH2 domain, a CH3 domain, and a CH4 domain and an immunoglobulin hinge region (or a part of the hinge region); and 6) a dimer between each domain of the heavy chain constant region and the light chain constant region, but is not limited thereto.

Additionally, in a specific embodiment, the immunoglobulin Fc region may be in a dimeric form and one molecule of X may be covalently linked to one Fc region in a dimer form, where the immunoglobulin Fc and X may be linked to each other by a non-peptide polymer. Meanwhile, it is also possible that two molecules of X are symmetrically linked to a Fc region in a dimer form. However, the linkage is not limited thereto.

Additionally, the immunoglobulin Fc region of the present invention not only includes a native amino acid sequence but also a sequence derivative thereof. An amino acid sequence derivative refers to an amino acid sequence which has a difference in at least one amino acid residue due to deletion, insertion, non-conservative or conservative substitution, or a combination thereof.

For example, the amino acid residues at positions 214 to 238, 297 to 299, 318 to 322, or 327 to 331, which are known to be in the conjugation of an immunoglobulin Fc, may be used as suitable sites for modification.

Additionally, other various derivatives are possible, including one that has a deletion of a region capable of forming a disulfide bond, or a deletion of some amino acid residues at the N-terminus of native Fc or an addition of a methionine residue at the N-terminus of native Fc. Further, to remove effector functions, a deletion may occur in a complement-binding site, such as a C1q-binding site and an antibody dependent cell mediated cytotoxicity (ADCC) site. Techniques of preparing such sequence derivatives of the immunoglobulin Fc region are disclosed in International Patent Publication Nos. WO 97/34631, WO 96/32478, etc.

Amino acid exchanges in proteins and peptides, which do not entirely alter the activity of the proteins or peptides, are known in the art (H. Neurath, R. L. Hill, *The Proteins*, Academic Press, New York, 1979). The most commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly, in both directions. Depending on the cases, the Fc region may be modified by phosphorylation, sulfation, acrylation, glycosylation, methylation, farnesylation, acetylation, amidation, etc.

The above-described Fc derivatives show a biological activity identical to that of the Fc region of the present invention and they may have improved structural stability against heat, pH, etc.

Further, the immunoglobulin Fc region may be obtained from native forms isolated in vivo from humans or animals such as cows, goats, pigs, mice, rabbits, hamsters, rats, guinea pigs, etc., or may be recombinant immunoglobulin Fc region obtained from transformed animal cells or microorganisms or derivatives thereof. Herein, the Fc region may be obtained from a native immunoglobulin by isolating a whole immunoglobulin from a living human or animal body and treating the isolated immunoglobulin with protease. When the whole immunoglobulin is treated with papain, it is cleaved into Fab and Fc regions, whereas when the whole immunoglobulin is treated with pepsin, it is cleaved into pF'c and F(ab)$_2$ fragments. Fc or pF'c can be isolated using size exclusion chromatography, etc. In a more specific embodiment, the immunoglobulin Fc region is a recombinant immunoglobulin Fc region obtained from a microorganism expressing a human-derived Fc region.

In addition, the immunoglobulin Fc region may be in the form of natural glycans, increased or decreased glycans compared to the native type, or in a deglycosylated form. The increase, decrease, or removal of the immunoglobulin Fc glycans may be achieved by conventional methods such as a chemical method, an enzymatic method, and a genetic engineering method using a microorganism. The immunoglobulin Fc region obtained by removal of glycans from the Fc region shows a significant decrease in binding affinity to the C1q and a decrease or loss in antibody-dependent cytotoxicity or complement-dependent cytotoxicity, and thus it does not induce unnecessary immune responses in vivo. In this regard, an immunoglobulin Fc region in a deglycosylated or aglycosylated immunoglobulin Fc region may be a more suitable form to meet the original object of the present invention as a drug carrier. As used herein, the term "deglycosylation" refers to enzymatically removing sugar moieties from an Fc region, and the term "aglycosylation" refers to an unglycosylated Fc region produced in prokaryotes, more specifically, *E. coli*.

Meanwhile, the immunoglobulin Fc region may be derived from humans or other animals including cows, goats, pigs, mice, rabbits, hamsters, rats, and guinea pigs. In a more specific embodiment, it is derived from humans.

In addition, the immunoglobulin (Ig) Fc region may be derived from IgG, IgA, IgD, IgE, IgM, or a combination or hybrid thereof. In a more specific embodiment, it is derived from IgG or IgM, which are among the most abundant proteins in human blood, and in an even more specific embodiment, it is derived from IgG, which is known to enhance the half-lives of ligand-binding proteins. In a yet even more specific embodiment, the immunoglobulin Fc region is an IgG4 Fc region, and in the most specific embodiment, the IgG4 Fc region is an aglycosylated Fc region derived from human IgG4, but is not limited thereto.

In particular, as used herein, the term "combination" means that polypeptides encoding single-chain immunoglobulin Fc regions of the same origin are linked to a single-chain polypeptide of a different origin to form a dimer or multimer. That is, a dimer or multimer may be formed from two or more fragments selected from the group consisting of IgG Fc, IgA Fc, IgM Fc, IgD Fc, and IgE Fc fragments.

Additionally, the above conjugate may have an improved long-acting property of the effect compared to native GLP-1, GIP, or glucagon, or compared to the X where the F is not modified, and these conjugates include those enclosed by biodegradable nanoparticles in addition to those described above.

Another aspect of the present invention provides a polynucleotide encoding the conjugate, a vector including the polynucleotide, and a transformant including the polynucleotide or a vector including the polynucleotide.

The conjugate is the same as explained above.

The polynucleotide may be one that encodes a conjugate in the form of a fusion protein.

Additionally, the isolated polynucleotide encoding the conjugate includes, within the scope of the present invention, a polynucleotide sequence having a sequence identity to the corresponding sequence of 75% or higher, specifically 85% or higher, more specifically 90% or higher, and even more specifically 95% or higher.

As used herein, the term "homology" indicates sequence similarity with a wild-type amino acid sequence or wild-type nucleic acid sequence, and the homology comparison may be done with the naked eye or using a commercially-available comparison program. Using a commercially available computer program, the homology between two or more sequences may be expressed as a percentage (%), and the homology (%) between adjacent sequences may be calculated.

As used herein, the term "recombinant vector" refers to a DNA construct in which the polynucleotide encoding the target protein, e.g., the conjugate is operably linked to an appropriate regulatory sequence to enable the expression of the target protein, the conjugate, in a host cell.

The regulatory sequence includes a promoter capable of initiating transcription, any operator sequence for regulating the transcription, a sequence encoding an appropriate mRNA ribosome-binding domain, and a sequence for regulating the termination of transcription and translation. The recombinant vector, after being transformed into a suitable host cell, may be replicated or function irrespective of the host genome, or may be integrated into the host genome itself.

The recombinant vector used in the present invention may not be particularly limited as long as the vector is replicable in the host cell, and it may be constructed using any vector known in the art. Examples of the vector conventionally used may include natural or recombinant plasmids, cosmids, viruses, and bacteriophages. The vectors to be used in the present invention are not particularly limited but any expression vector known in the art may be used.

The recombinant vector is used for the transformation of a host cell for producing the conjugate of the present invention. Additionally, these transformed cells, as a part of the present invention, may be used for amplifying nucleic acid fragments and vectors, or they may be cultured cells or cell lines used in the recombinant production of the conjugate of the present invention.

As used herein, the term "transformation" refers to a process of introducing a recombinant vector including a polynucleotide encoding a target protein into a host cell, thereby enabling the expression of the protein encoded by the polynucleotide in the host cell. For the transformed polynucleotide, it does not matter whether it is inserted into the chromosome of a host cell and located thereon or located outside of the chromosome, as long as it can be expressed in the host cell, and both cases are included.

Additionally, the polynucleotide includes DNA and RNA which encode the target protein. The polynucleotide may be introduced in any form as long as it can be introduced into a host cell and expressed therein. For example, the polynucleotide may be introduced into a host cell in the form of an expression cassette, which is a gene construct including all of the essential elements required for self-expression. The expression cassette may conventionally include a promoter operably linked to the polynucleotide, a transcription termination signal, a ribosome-binding domain, and a translation termination signal. The expression cassette may be in the form of an expression vector capable of self-replication. Additionally, the polynucleotide may be introduced into a host cell as it is and operably linked to a sequence essential for its expression in the host cell, but is not limited thereto.

Additionally, as used herein, the term "operably linked" refers to a functional connection between a promoter sequence, which initiates and mediates the transcription of the polynucleotide encoding the target protein, i.e., a conjugate of the present invention, and the above gene sequence.

An appropriate host to be used in the present invention may not be particularly limited as long as it can express the polynucleotide of the present invention. Examples of the appropriate host may include bacteria belonging to the genus *Escherichia* such as *E. coli*; bacteria belonging to the genus *Bacillus* such as *Bacillus subtilis*; bacteria belonging to the genus *Pseudomonas* such as *Pseudomonas putida*; yeasts such as *Pichia pastoris, Saccharomyces cerevisiae*, and *Schizosaccharomyces pombe*; insect cells such as *Spodoptera frugiperda* (Sf9), and animal cells such as CHO, COS, and BSC.

Still another aspect of the present invention provides a composition containing the conjugate.

The conjugate is the same as explained above.

Specifically, the composition may be a pharmaceutical composition, and more specifically, a pharmaceutical composition for preventing or treating metabolic syndrome.

As used herein, the term "prevention" refers to all activities that inhibit or delay metabolic syndrome by administering the above conjugate or composition containing the conjugate, and the term "treatment" refers to all activities that improve or advantageously change the symptoms of metabolic syndrome by administering the above conjugate or composition containing the conjugate.

As used herein, the term "administration" refers to the introduction of a particular substance into a subject by an appropriate method, and the administration route of the composition may be any conventional route that enables delivery of the composition to the target in vivo, for example, intraperitoneal administration, intravenous administration, intramuscular administration, subcutaneous administration, intradermal administration, oral administration, topical administration, intranasal administration, intrapulmonary administration, intrarectal administration, etc.

As used herein, the term "metabolic syndrome" refers to a symptom where various diseases that occur due to chronic metabolic disorder occur alone or in combination. In particular, examples of diseases that belong to metabolic syndrome may include impaired glucose tolerance, hypercholesterolemia, dyslipidemia, obesity, diabetes, hypertension, arteriosclerosis due to dyslipidemia, atherosclerosis, arteriosclerosis, and coronary heart disease, but are not limited thereto.

As used herein, the term "obesity" refers to a medical condition with excess body fat accumulation and people are generally defined to be obese when their body mass index (BMI; a value of body mass (kg) over body height squared (m)) is 25 or higher. Obesity is most commonly caused by energy imbalance due to excessive food intake compared to energy consumption over a long period of time. Obesity, being a metabolic disease that affects the entire body, increases the possibility of developing of diabetes and hyperlipidemia, increases the risk of the incidence of sexual dysfunction, arthritis, and cardiovascular disease, and is associated with cancer development in some cases.

The pharmaceutical composition of the present invention may further contain a pharmaceutically acceptable carrier, excipient, or diluent. The pharmaceutically acceptable carrier, excipient, or diluent may be non-naturally occurring.

As used herein, the term "pharmaceutically acceptable" refers to the properties of having a sufficient amount to exhibit a therapeutic effect and not causing adverse effects, and may be easily determined by a skilled person in the art based on the factors well-known in the medical field, such as the kind of disease, age, body weight, health status, sex, drug sensitivity of a patient, administration route, administration method, administration frequency, duration of treatment, a drug(s) to be mixed or administered simultaneously, etc.

The pharmaceutical composition of the present invention containing the peptide of the present invention may further contain a pharmaceutically acceptable carrier. The pharmaceutically acceptable carrier may include, for oral administration, a binder, a lubricant, a disintegrant, an excipient, a solubilizing agent, a dispersant, a stabilizing agent, a suspending agent, a coloring agent, a flavoring agent, etc.; for injections, a buffering agent, a preserving agent, an analgesic, a solubilizing agent, an isotonic agent, a stabilizing agent, etc., which may be combined to be used; and for topical administrations, a base, an excipient, a lubricant, a preserving agent, etc.

The formulation type of the composition according to the present invention may be prepared variously by combining with a pharmaceutically acceptable carrier described above. For example, for oral administration, the composition may be formulated into tablets, troches, capsules, elixirs, suspensions, syrups, wafers, etc. For injections, the composition may be formulated into unit-dose ampoules or multi-dose containers. The composition may also be formulated into solutions, suspensions, tablets, pills, capsules, sustained-release formulations, etc.

Meanwhile, examples of suitable carriers, excipients, and diluents may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, etc. Additionally, the composition may further contain a filler, an anti-coagulant, a lubricant, a humectant, a flavoring agent, a preservative, etc.

Additionally, the pharmaceutical composition of the present invention may be prepared in any formulation type selected from the group consisting of tablets, pills, powders, granules, capsules, suspensions, liquid medicine for internal use, emulsions, syrups, sterile aqueous solutions, non-aqueous solvents, lyophilized formulations, and suppositories.

Additionally, the composition may be formulated into a unit dosage form suitable for the patient's body, and is specifically formulated into a preparation useful for protein drugs according to the typical method in the pharmaceutical field so as to be administered by an oral or parenteral route, such as through skin, intravenously, intramuscularly, intraarterially, intramedullarily, intrathecally, intraventricularly, pulmonarily, transdermally, subcutaneously, intraperitoneally, intranasally, intragastrically, topically, sublingually, vaginally, or rectally, but is not limited thereto.

Additionally, the conjugate may be used by mixing with various pharmaceutically acceptable carriers approved as pharmaceutical drugs such as physiological saline or organic solvents. For increasing stability or absorptivity, carbohydrates such as glucose, sucrose, or dextrans, antioxidants such as ascorbic acid or glutathione, chelating agents, low molecular weight proteins, or other stabilizers may be used as pharmaceutical drugs.

The administration dose and frequency of the pharmaceutical composition of the present invention are determined by the type of active ingredient(s), together with various factors such as the disease to be treated, administration route, patient's age, gender, and body weight, and severity of the disease.

The total effective dose of the composition of the present invention may be administered to a patient in a single dose or may be administered for a long period of time in multiple doses according to a fractionated treatment protocol. In the pharmaceutical composition of the present invention, the content of active ingredient(s) may vary depending on the disease severity. Specifically, the total daily dose of the conjugate of the present invention may be about 0.0001 mg to 500 mg per 1 kg of body weight of a patient. However, the effective dose of the conjugate is determined considering various factors including patient's age, body weight, health conditions, gender, disease severity, diet, and excretion rate, in addition to administration route and treatment frequency of the pharmaceutical composition. In this regard, those skilled in the art may easily determine the effective dose suitable for the particular use of the pharmaceutical composition of the present invention. The pharmaceutical composition according to the present invention is not particularly limited to the formulation and administration route and mode, as long as it shows the effects of the present invention.

The pharmaceutical composition of the present invention shows excellent in vivo duration of efficacy and titer, and thus the number and frequency of administration of the pharmaceutical preparation of the present invention can be significantly reduced.

Still another aspect of the present invention provides a method for treating a target disease, which includes administering the conjugate or a composition containing the conjugate to a subject in need thereof. The target disease may be a metabolic syndrome.

The conjugate or composition containing the conjugate are the same as explained above. The target disease may be a metabolic syndrome.

As used herein, the term "subject" refers to a subject suspected of having a metabolic syndrome, and the subject suspected of having a metabolic syndrome refers to mammals including humans, rats, cattle, etc., which have or are at the risk of developing the metabolic syndrome, but any subject which can be treated with the conjugate of the present invention or the composition containing the conjugate is included without limitation.

The method of the present invention may include administering a pharmaceutically effective amount of the pharmaceutical composition containing the conjugate. The total daily dose of the composition may be determined within the scope of appropriate medical judgment by a physician, and the composition may be administered once or several times in divided doses a day. However, for the purpose of the present invention, the specific therapeutically effective dose of the composition for any particular patient is preferably applied differently depending on various factors including the kind and degree of response to be achieved, specific compositions including whether other agents are occasionally used therewith, the patient's age, body weight, health condition, gender and diet, the time and route of administration, the secretion rate of the composition, the duration of treatment, other drugs used in combination or simultaneously with the specific compositions, and similar factors well-known in the medical field.

Still another aspect of the present invention provides the use of the conjugate or composition containing the conjugate in the preparation of a medicament.

The conjugate or composition containing the conjugate is the same as explained above.

The medicament may be for preventing or treating metabolic syndrome.

Hereinafter, the present invention will be described in more detail with reference to the following Examples. However, these Examples are for illustrative purposes only, and the invention is not intended to be limited by these Examples.

Example 1: Preparation of Triple Agonists

Triple agonists showing activities to all of GLP-1, GIP, and glucagon receptors were prepared and their amino acid sequences are shown in Table 1 below.

TABLE 1

| SEQ ID NO | Sequence | Information |
|---|---|---|
| 1 | H X Q G T F T S D V S S Y L D G Q A A K E F I A W L V K G C | |
| 2 | H X Q G T F T S D V S S Y L D G Q A Q K E F I A W L V K G C | |
| 3 | H X Q G T F T S D V S S Y L L G Q A A K Q F I A W L V K G G P S S G A P P P S C | |
| 4 | H X Q G T F T S D V S S Y L L G Q Q K E F I A W L V K G C | |
| 5 | H X Q G T F T S D V S S Y L L G Q Q Q K E F I A W L V K G G P S S G A P P P S C | |
| 6 | H X Q G T F T S D V S S Y L D G Q A A K E F V A W L L K G C | |
| 7 | H X Q G T F T S D V S K Y L D G Q A A K E F V A W L L K G C | |
| 8 | H X Q G T F T S D V S K Y L D G Q A A Q E F V A W L L K G C | |
| 9 | H X Q G T F T S D V S K Y L D G Q A A Q E F V A W L L A G C | |
| 10 | H X Q G T F T S D V S K Y L D G Q A A Q E F V A W L L A G G P S S G A P P P S C | |
| 11 | C A G E G T F T S D L S K Y L D S R R Q Q L F V Q W L K A G G P S S G A P P P S H G | |
| 12 | C A G E G T F I S D L S K Y M D E Q A V Q L F V E W L M A G G P S S G A P P P S H G | |
| 13 | C A G E G T F I S D Y S I Q L D E I A V Q D F V E W L L A Q K P S S G A P P P S H G | |
| 14 | C A G Q G T F T S D Y S I Q L D E I A V R D F V E W L K N G G P S S G A P P P S H G | |
| 15 | C A G Q G T F T S D L S K Q M D E E A V R L F I E W L K N G G P S S G A P P P S H G | |
| 16 | C A G Q G T F T S D L S K Q M D S E A Q Q L F I E W L K N G G P S S G A P P P S H G | |
| 17 | C A G Q G T F T S D L S K Q M D E E R A R E F I E W L L A Q K P S S G A P P P S H G | |

TABLE 1-continued

| SEQ ID NO | Sequence | Information |
|---|---|---|
| 18 | CAGQGTFTSDLSKQMDSERAREFIEWLKNTGPSSGAPPPSHG | |
| 19 | CAGQGTFTSDLSIQYDSEHQRDFIEWLKDTGPSSGAPPPSHG | |
| 20 | CAGQGTFTSDLSIQYEEEAQQDFVEWLKDTGPSSGAPPPSHG | |
| 21 | YXQGTFTSDYSKYLD<u>E</u>CRA<u>K</u>EFVQWLLDHHPSSGQPPPS | Ring formation |
| 22 | YXQGTFTSDYSKCLD<u>E</u>KRA<u>K</u>EFVQWLLDHHPSSGQPPPS | Ring formation |
| 23 | YXQGTFTSDYSKYLD<u>E</u>CRA<u>K</u>EFVQWLLAQKGKKNDWKHNIT | Ring formation |
| 24 | YXQGTFTSDYSKYLD<u>E</u>CRA<u>K</u>EFVQWLKNGGPSSGAPPPS | Ring formation |
| 25 | HXQGTFTSDCSKYLD<u>E</u>RAAQDFVQWLLDGGPSSGAPPPS | |
| 26 | HXQGTFTSDCSKYLDSRAAQDFVQWLLDGGPSSGAPPPS | |
| 27 | HXQGTFTSDYSKYLD<u>E</u>RACQDFVQWLLDQGGPSSGAPPPS | |
| 28 | HXQGTFTSDYSKYLD<u>E</u>KRAQEFVCWLLAQKGKKNDWKHNIT | |
| 29 | HXQGTFTSDYSKYLD<u>E</u>KAA<u>K</u>EFVQWLLNTC | Ring formation |
| 30 | HXQGTFTSDYSKYLD<u>E</u>KAQ<u>K</u>EFVQWLLDTC | Ring formation |
| 31 | HXQGTFTSDYSKYLD<u>E</u>KAC<u>K</u>EFVQWLLAQ | Ring formation |
| 32 | HXQGTFTSDYSKYLD<u>E</u>KAC<u>K</u>DFVQWLLDGGPSSGAPPPS | Ring formation |
| 33 | HXQGTFTSDYSIAMD<u>E</u>IHQ<u>K</u>DFVNWLLAQKC | Ring formation |
| 34 | HXQGTFTSDYSKYLD<u>E</u>KRQ<u>K</u>EFVNWLLAQKC | Ring formation |
| 35 | HXQGTFTSDYSIAMD<u>E</u>IHQ<u>K</u>DFVNWLLNTKC | Ring formation |
| 36 | HXQGTFTSDYSKYLC<u>E</u>KRQ<u>K</u>EFVQWLLNGGPSSGAPPPSG | Ring formation |
| 37 | HXQGTFTSDYSKYLD<u>E</u>CRQ<u>K</u>EFVQWLLNGGPSSGAPPPSG | Ring formation |
| 38 | CAXQGTFTSDKSSYLDERAAQDFVQWLLDGGPSSGAPPPSS | |
| 39 | HXQGTFTSDYSKYLDGQHAQCFVAWLLAGGGPSSGAPPPS | |
| 40 | HXQGTFTSDKSYLDERACQDFVQWLLDGGPSSGAPPPS | |
| 41 | HXQGTFTSDKSYLDECAAQDFVQWLLDGGPSSGAPPPS | |
| 42 | YXQGTFTSDYSKYLD<u>E</u>KRA<u>K</u>EFVQWLLDHHPSSGQPPPSC | Ring formation |

TABLE 1-continued

| SEQ ID NO | Sequence | Information |
|---|---|---|
| 43 | Y X Q G T F T S D Y S K Y L D E K R A K E F V Q W L L D H H C S S G Q P P P S | Ring formation |
| 44 | H G Q G T F T S D C S K Q L D G Q A A Q E F V A W L L A G G P S S G A P P P S | |
| 45 | H G Q G T F T S D C S K Y M D G Q A A Q D F V A W L L A G G P S S G A P P P S | |
| 46 | H G Q G T F T S D C S K Y L D E Q H A Q E F V A W L L A G G P S S G A P P P S | |
| 47 | H G Q G T F T S D C S K Y L D G Q R A Q E F V A W L L A G G P S S G A P P P S | |
| 48 | H G Q G T F T S D C S K Y L D G Q R A Q D F V N W L L A G G P S S G A P P P S | |
| 49 | C A X Q G T F T S D Y S I C M D E I H Q K D F V N W L L N T K | Ring formation |
| 50 | H X Q G T F T S D Y S K Y L D E K R A K E F V Q W L L D H H P S S G Q P P P S C | Ring formation |
| 51 | H X Q G T F T S D Y S K Y L D E K R Q K E F V Q W L L N T C | Ring formation |
| 52 | H X Q G T F T S D Y S K Y L D E K R Q K E F V Q W L L D T C | Ring formation |
| 53 | H X E G T F T S D Y S I A M D E I H Q K D F V N W L L A Q C | Ring formation |
| 54 | H X E G T F T S D Y S I A M D E I H Q K D F V D W L L A E C | Ring formation |
| 55 | H X Q G T F T S D Y S I A M D E I H Q K D F V N W L L A Q C | Ring formation |
| 56 | H X Q G T F T S D Y S K Y L D E K R Q K E F V N W L L A Q C | Ring formation |
| 57 | H X Q G T F T S D Y S I A M D E I H Q K D F V N W L L N T C | Ring formation |
| 58 | H X Q G T F T S D Y S K Y L D E K R Q K E F V Q W L L N T K C | Ring formation |
| 59 | C A X Q G T F T S D Y S I C M D E K H Q K D F V N W L L N T K | Ring formation |
| 60 | C A X Q G T F T S D Y S I A M D E K H C K D F V N W L L N T K | Ring formation |
| 61 | C A X Q G T F T S D Y S I A M D E I A C K D F V N W L L N T K | Ring formation |
| 62 | C A X Q G T F T S D K S K Y L D E R A A Q D F V Q W L L D G G P S S G A P P P S | |
| 63 | C A X Q G T F T S D C S K Y L D E R A A Q D F V Q W L L D G G P S S G A P P P S | |
| 64 | Y X Q G T F T S D Y S K Y L D E C A A K E F V Q W L L D H H P S S G Q P P P S | Ring formation |
| 65 | H X Q G T F T S D Y S K C L D E K R A K E F V Q W L L D H H P S S G Q P P P S | Ring formation |
| 66 | Y X Q G T F T S D Y S K Y L D E C R A K D F V Q W L L D H H P S S G Q P P P S | Ring formation |
| 67 | Y X Q G T F T S D Y S K Y L D E C A A K D F V Q W L L D H H P S S G Q P P P S | Ring formation |

TABLE 1-continued

| SEQ ID NO | Sequence | Information |
|---|---|---|
| 68 | Y X Q G T F T S D Y S K C L D E K A A K E F V Q W L L D H H P S S G Q P P P S | Ring formation |
| 69 | Y X Q G T F T S D Y S K C L D E R A A K E F V Q W L L D H H P S S G Q P P P S | Ring formation |
| 70 | Y X Q G T F T S D Y S K C L D E K R A K D F V Q W L L D H H P S S G Q P P P S | Ring formation |
| 71 | Y X Q G T F T S D Y S K Y L D E R A C K D F V Q W L L D H H P S S G Q P P P S | Ring formation |
| 72 | Y X Q G T F T S D C S K Y L D E R A A K D F V Q W L L D H H P S S G Q P P P S | Ring formation |
| 73 | C A X Q G T F T S D Y S K Y L D E C R A K E F V Q W L L D H H P S S G Q P P P S | Ring formation |
| 74 | C A X Q G T F T S D Y S K C L D E K R A K E F V Q W L L D H H P S S G Q P P P S | Ring formation |
| 75 | Y X Q G T F T S D Y S K Y L D E K A A K E F V Q W L L D H H P S S G Q P P P S C | Ring formation |
| 76 | Y X Q G T F T S D Y S K Y L D E K R A K D F V Q W L L D H H P S S G Q P P P S C | Ring formation |
| 77 | Y X Q G T F T S D Y S K Y L D E K A A K D F V Q W L L D H H P S S G Q P P P S C | Ring formation |
| 78 | H X Q G T F T S D Y S K Y L D E K R Q K E F V Q W L L D T K C | Ring formation |
| 79 | H X E G T F T S D Y S I A M D E I H Q K D F V N W L L A Q K C | Ring formation |
| 80 | H X E G T F T S D Y S I A M D E I H Q K D F V D W L L A E K C | Ring formation |
| 81 | C A X Q G T F T S D Y S K Y L D E K R Q K E F V Q W L L N T C | Ring formation |
| 82 | C A X Q G T F T S D Y S K Y L D E K R Q K E F V Q W L L D T C | Ring formation |
| 83 | C A X E G T F T S D Y S I A M D E I H Q K D F V N W L L A Q C | Ring formation |
| 84 | C A X E G T F T S D Y S I A M D E I H Q K D F V D W L L A E C | Ring formation |
| 85 | C A X Q G T F T S D Y S I A M D E I H Q K D F V N W L L A Q C | Ring formation |
| 86 | C A X Q G T F T S D Y S K Y L D E K R Q K E F V N W L L A Q C | Ring formation |
| 87 | C A X Q G T F T S D Y S I A M D E I H Q K D F V N W L L N T C | Ring formation |
| 88 | C A X Q G T F T S D Y S K Y L D E K R Q K E F V Q W L L N T K C | Ring formation |
| 89 | C A X Q G T F T S D Y S K Y L D E K R Q K E F V Q W L L D T K C | Ring formation |
| 90 | C A X E G T F T S D Y S I A M D E I H Q K D F V N W L L A Q K C | Ring formation |
| 91 | C A X E G T F T S D Y S I A M D E I H Q K D F V D W L L A E K C | Ring formation |
| 92 | C A X Q G T F T S D Y S I A M D E I H Q K D F V N W L L A Q K C | Ring formation |

TABLE 1-continued

| SEQ ID NO | Sequence | Information |
|---|---|---|
| 93 | C A X Q G T F T S D Y S K Y L D <u>E</u> K R Q <u>K</u> E F V N W L L A Q K C | Ring formation |
| 94 | C A X Q G T F T S D Y S I A M D <u>E</u> I H Q <u>K</u> D F V N W L L N T K C | Ring formation |
| 95 | Y X Q G T F T S D Y S K Y L D <u>E</u> K R A <u>K</u> E F V Q W L L C H H P S S G Q P P P S | Ring formation |
| 96 | Y X Q G T F T S D Y S K Y L D <u>E</u> K R A <u>K</u> E F V Q W L L D H C P S S G Q P P P S | Ring formation |
| 97 | Y X Q G T F T S D Y S K Y L D <u>E</u> K R A <u>K</u> E F V Q W L L D C H P S S G Q P P P S | Ring formation |
| 98 | Y X Q G T F T S D Y S K A L D <u>E</u> K A A <u>K</u> E F V N W L L D H H P S S G Q P P P S C | Ring formation |
| 99 | Y X Q G T F T S D Y S K A L D <u>E</u> K A A <u>K</u> D F V N W L L D H H P S S G Q P P P S C | Ring formation |
| 100 | Y X Q G T F T S D Y S K A L D <u>E</u> K A A <u>K</u> E F V Q W L L D Q H P S S G Q P P P S C | Ring formation |
| 101 | Y X Q G T F T S D Y S K A L D <u>E</u> K A A <u>K</u> E F V N W L L D Q H P S S G Q P P P S C | Ring formation |
| 102 | Y X Q G T F T S D Y S K A L D <u>E</u> K A A <u>K</u> D F V N W L L D Q H P S S G Q P P P S C | Ring formation |

In the sequences described in Table 1, the amino acid represented by X represents aminoisobutyric acid (Aib), which is a non-natural amino acid, and the underlined amino acids represent the formation of a ring between the underlined amino acids. Additionally, in Table 1, CA represents 4-imidazoacetyl and Y represents tyrosine.

Example 2: Preparation of Long-Acting Conjugates of Triple Agonists

For the pegylation of the cysteine residue of triple agonists (SEQ ID NOS: 21, 22, 42, 43, 50, 77, and 96) of Example 1 using PEG (10 kDa) having a maleimide group and an aldehyde group at both ends, respectively, i.e., maleimide-PEG-aldehyde (10 kDa, NOF, Japan), the triple agonists and the maleimide-PEG-aldehyde were reacted at a molar ratio of 1:1 to 3, at a protein concentration of 1 mg/mL to 5 mg/mL at low temperature for 0.5 to 3 hours. In particular, the reaction was conducted in an environment in which 20% to 60% isopropanol was added to 50 mM Tris buffer (pH 7.5). Upon completion of the reaction, the reactants were applied to SP sepharose HP (GE healthcare, USA) to purify the triple agonists, which is mono-pegylated on cysteine residue thereof.

Then, the purified mono-pegylated triple agonists and an immunoglobulin Fc were reacted at a molar ratio of 1:1 to 5, at a protein concentration of 10 mg/mL to 50 mg/mL at 4° C. to 8° C. for 12 hours to 18 hours. The reaction was conducted in an environment in which 10 mM to 50 mM sodium cyanoborohydride (NaCNBH₃), i.e., a reducing agent, and 10% to 30% isopropanol were added to 100 mM potassium phosphate butter (pH 6.0). Upon completion of the reaction, the reactants were applied to the Butyl sepharose FF purification column (GE healthcare, USA) and Source ISO purification column (GE healthcare, USA) to purify the conjugate including the triple agonists and the immunoglobulin Fc.

After preparation, the purity analyzed by reverse phase chromatography, size exclusion chromatography, and ion exchange chromatography was shown to be 95% or higher.

In particular, the conjugate in which the triple agonist of SEQ ID NO: 21 and an immunoglobulin Fc were linked by PEG was named as "the conjugate including the triple agonist of SEQ ID NO: 21 and an immunoglobulin Fc" or "long-acting conjugate of SEQ ID NO: 21", and they can be interchangeably used in the present invention.

In particular, the conjugate in which the triple agonist of SEQ ID NO: 22 and an immunoglobulin Fc were linked by PEG was named as "the conjugate including the triple agonist of SEQ ID NO: 22 and an immunoglobulin Fc" or "long-acting conjugate of SEQ ID NO: 22", and they can be interchangeably used in the present invention.

In particular, the conjugate in which the triple agonist of SEQ ID NO: 42 and an immunoglobulin Fc were linked by PEG was named as "the conjugate including the triple agonist of SEQ ID NO: 42 and an immunoglobulin Fc" or "long-acting conjugate of SEQ ID NO: 42", and they can be interchangeably used in the present invention.

In particular, the conjugate in which the triple agonist of SEQ ID NO: 43 and an immunoglobulin Fc were linked by PEG was named as "the conjugate including the triple agonist of SEQ ID NO: 43 and an immunoglobulin Fc" or "long-acting conjugate of SEQ ID NO: 43", and they can be interchangeably used in the present invention.

In particular, the conjugate in which the triple agonist of SEQ ID NO: 50 and an immunoglobulin Fc were linked by PEG was named as "the conjugate including the triple agonist of SEQ ID NO: 50 and an immunoglobulin Fc" or "long-acting conjugate of SEQ ID NO: 50", and they can be interchangeably used in the present invention.

In particular, the conjugate in which the triple agonist of SEQ ID NO: 77 and an immunoglobulin Fc were linked by PEG was named as "the conjugate including the triple agonist of SEQ ID NO: 77 and an immunoglobulin Fc" or "long-acting conjugate of SEQ ID NO: 77", and they can be interchangeably used in the present invention.

In particular, the conjugate in which the triple agonist of SEQ ID NO: 96 and an immunoglobulin Fc were linked by PEG was named as "the conjugate including the triple agonist of SEQ ID NO: 96 and an immunoglobulin Fc" or "long-acting conjugate of SEQ ID NO: 96", and they can be interchangeably used in the present invention.

Experimental Example 1: Measurement of In Vitro Activities of Triple Agonists and Long-Acting Conjugates Thereof The activities of the triple agonists and long-acting conjugates thereof prepared in Examples 1 and 2 were measured by a method of measuring in vitro cellular activities using cell lines, where a GLP-1 receptor, a glucagon (GCG) receptor, and a GIP receptor are transformed, respectively.

Each of the cell lines above is one in which the genes for human GLP-1 receptor, human GCG receptor, and human GIP receptor were transformed in Chinese hamster ovary (CHO), respectively, and can be expressed therein, and is thus suitable for the measurement of the activities of GLP-1, GCG, and GIP. Accordingly, the activity for each part was measured using the respective transformed cell line.

For the measurement of the GLP-1 activities of the triple agonists and long-acting conjugates prepared in Examples 1 and 2, human GLP-1 was subjected to a 4-fold serial dilution from 50 nM to 0.000048 nM, and the triple agonists and long-acting conjugates thereof prepared in Examples 1 and 2 were subjected to a 4-fold serial dilution from 400 nM to 0.00038 nM. The culture solution was removed from the cultured CHO cells, in which the human GLP-1 receptor was expressed, and each of the serially-diluted materials was added to the CHO cells in an amount of 5 µL, respectively. Then, a buffer solution containing cAMP antibody was added thereto in an amount of 5 µL and cultured at room temperature for 15 minutes. Then, a detection mix containing a cell lysis buffer was added thereto in an amount of 10 µL for the lysis of the cells and reacted at room temperature for 90 minutes. The cell lysates, upon completion of the reaction, were applied to LANCE cAMP kit (PerkinElmer, USA) to calculate the $EC_{50}$ value via accumulated cAMP, and the values were compared with each other. The relative potencies compared to human GLP-1 are shown in Tables 2 and 3 below.

For the measurement of the GCG activities of the triple agonists and long-acting conjugates prepared in Examples 1 and 2, human GCG was subjected to a 4-fold serial dilution from 50 nM to 0.000048 nM, and the triple agonists and long-acting conjugates thereof prepared in Examples 1 and 2 were subjected to a 4-fold serial dilution from 400 nM to 0.00038 nM. The culture solution was removed from the cultured CHO cells, in which the human GCG receptor was expressed, and each of the serially-diluted materials was added to the CHO cells in an amount of 5 µL, respectively. Then, a buffer solution containing cAMP antibody was added thereto in an amount of 5 µL and cultured at room temperature for 15 minutes. Then, a detection mix containing a cell lysis buffer was added thereto in an amount of 10 µL for the lysis of the cells and reacted at room temperature for 90 minutes. The cell lysates, upon completion of the reaction, were applied to LANCE cAMP kit (PerkinElmer, USA) to calculate the $EC_{50}$ value via accumulated cAMP, and the values were compared with each other. The relative potencies compared to human GCG are shown in Tables 2 and 3 below.

For the measurement of the GIP activities of the triple agonists and long-acting conjugates prepared in Examples 1 and 2, human GIP was subjected to a 4-fold serial dilution from 50 nM to 0.000048 nM, and the triple agonists and long-acting conjugates thereof prepared in Examples 1 and 2 were subjected to a 4-fold serial dilution from 400 nM to 0.00038 nM. The culture solution was removed from the cultured CHO cells, in which the human GIP receptor was expressed, and each of the serially-diluted materials was added to the CHO cells in an amount of 5 µL, respectively. Then, a buffer solution containing cAMP antibody was added thereto in an amount of 5 µL and cultured at room temperature for 15 minutes. Then, a detection mix containing a cell lysis buffer was added thereto in an amount of 10 µL for the lysis of the cells and reacted at room temperature for 90 minutes. The cell lysates, upon completion of the reaction, were applied to LANCE cAMP kit (PerkinElmer, USA) to calculate the $EC_{50}$ value via accumulated cAMP, and the values were compared with each other. The relative potencies compared to human GIP are shown in Tables 2 and 3 below.

TABLE 2

| | Relative potency ratio of triple agonists | | |
|---|---|---|---|
| SEQ ID NO: | In vitro activity compared to native peptide (%) | | |
| | vs. GLP-1 | vs. Glucagon | vs. GIP |
| 1 | 3.2 | <0.1 | <0.1 |
| 2 | 5.9 | <0.1 | <0.1 |
| 3 | 1.8 | <0.1 | <0.1 |
| 4 | 8.5 | <0.1 | <0.1 |
| 5 | 42.1 | <0.1 | <0.1 |
| 6 | 17.0 | <0.1 | <0.1 |
| 7 | 13.7 | <0.1 | <0.1 |
| 8 | 14.2 | 0.10 | <0.1 |
| 9 | 32.1 | 0.13 | <0.1 |
| 10 | 46.0 | <0.1 | <0.1 |
| 11 | 1.4 | <0.1 | <0.1 |
| 12 | 0.4 | <0.1 | <0.1 |
| 13 | <0.1 | <0.1 | <0.1 |
| 14 | 28.0 | <0.1 | <0.1 |
| 15 | 79.2 | <0.1 | <0.1 |
| 16 | 2.1 | <0.1 | <0.1 |
| 17 | 0.2 | <0.1 | <0.1 |
| 18 | <0.1 | <0.1 | <0.1 |
| 19 | <0.1 | <0.1 | <0.1 |
| 20 | <0.1 | <0.1 | <0.1 |
| 21 | 17.8 | 267 | 22.7 |
| 22 | 20.1 | 140 | 59.7 |
| 23 | 4.01 | 9.3 | <0.1 |
| 24 | 41.2 | 9.3 | <0.1 |
| 25 | 82.6 | 0.1 | <0.1 |
| 26 | 64.5 | 0.2 | <0.1 |
| 27 | 83.1 | 0.8 | 0.9 |
| 28 | 17.2 | 1.6 | <0.1 |
| 29 | 38.5 | 6.0 | <0.1 |
| 30 | 142 | 0.7 | 0.8 |
| 31 | 135 | 2.2 | 2.4 |
| 32 | 151 | 1.7 | 8.8 |
| 33 | 24.5 | <0.1 | 10.4 |
| 34 | 19.1 | 0.92 | 0.6 |
| 35 | 7.5 | <0.1 | 1.3 |
| 36 | 37.4 | 0.39 | 0.2 |
| 37 | 236 | 6.21 | 2.2 |
| 38 | 2.3 | — | — |
| 39 | 13.9 | 0.53 | <0.1 |
| 40 | 75.2 | <0.1 | <0.1 |
| 41 | 34.3 | <0.1 | <0.1 |
| 42 | 33.9 | 205.8 | 7.8 |
| 43 | 12.6 | 88.4 | 3.70 |

TABLE 2-continued

Relative potency ratio of triple agonists

| SEQ ID NO: | In vitro activity compared to native peptide (%) vs. GLP-1 | vs. Glucagon | vs. GIP |
|---|---|---|---|
| 44 | 1.3 | <0.1 | <0.1 |
| 45 | 6.6 | <0.1 | <0.1 |
| 46 | 1.4 | <0.1 | <0.1 |
| 47 | 2.4 | <0.1 | <0.1 |
| 48 | 1.5 | <0.1 | <0.1 |
| 49 | 29.8 | <0.1 | 3.3 |
| 50 | 67.4 | 50.5 | 2.7 |
| 51 | 14.4 | 2.0 | 0.1 |
| 52 | 44.1 | 7.5 | 0.3 |
| 53 | 161 | 8.4 | 1.3 |
| 54 | 30.6 | 1.4 | 0.1 |
| 55 | 27.1 | 0.7 | 2.4 |
| 56 | 57.9 | 4.9 | 0.8 |
| 57 | 11.7 | <0.1 | 0.3 |
| 58 | 39.1 | 2.6 | 0.2 |
| 59 | 40.3 | <0.1 | 4.0 |
| 60 | 106.2 | <0.1 | 8.2 |
| 61 | 59.8 | <0.1 | 2.8 |
| 62 | 5.2 | <0.1 | <0.1 |
| 63 | 15.3 | <0.1 | <0.1 |
| 64 | 64.6 | 60.1 | 92.9 |
| 65 | 95.4 | 25.2 | 11.6 |
| 66 | 15.8 | 172 | 17.2 |
| 67 | 28.5 | 46.2 | 39.8 |
| 68 | 27.9 | 8.8 | 107 |
| 69 | 24.3 | 9.6 | 62.8 |
| 70 | 15.1 | 71.3 | 64.4 |
| 71 | 90.1 | 12.7 | 94.7 |
| 72 | 11.5 | 1.0 | 1.6 |
| 73 | 22.6 | 5.4 | 3.0 |
| 74 | 12.9 | 0.9 | 1.0 |
| 75 | 35.1 | 8.5 | 18.0 |
| 76 | 10.3 | 47.6 | 11.7 |
| 77 | 38.7 | 12.2 | 35.5 |
| 78 | 51.0 | 14.0 | 0.12 |
| 79 | 41.5 | 4.9 | 1.4 |
| 80 | 8.1 | 0.0 | 0.1 |
| 81 | 7.8 | 0.3 | <0.1 |
| 82 | 9.5 | 1.1 | <0.1 |
| 83 | 47.3 | 1.3 | 0.4 |
| 84 | 4.2 | <0.1 | <0.1 |
| 85 | 4.3 | <0.1 | 0.3 |
| 86 | 28.4 | 0.4 | 0.2 |
| 87 | 0.9 | <0.1 | <0.1 |
| 88 | 9.6 | 0.3 | <0.1 |
| 89 | 7.1 | 0.7 | <0.1 |
| 90 | 7.4 | <0.1 | <0.1 |
| 91 | 31.9 | 16.8 | 0.3 |
| 92 | 0.8 | <0.1 | 0.4 |
| 93 | 5.7 | 0.3 | 0.7 |
| 94 | 0.5 | <0.1 | <0.1 |
| 95 | 2.1 | 0.4 | <0.1 |
| 96 | 34.4 | 194.8 | 5.2 |
| 97 | 10.5 | 62.8 | 2.6 |
| 98 | 28.1 | 8.2 | 47.1 |
| 99 | 20.9 | 14.9 | 57.7 |
| 100 | 42.2 | 12.7 | 118.5 |
| 101 | 23.2 | 13.9 | 40.1 |
| 102 | 23.3 | 29.5 | 58.0 |

TABLE 3

Relative potency ratio of long-acting conjugates of triple agonists

| Long-acting Conjugates | In vitro activity compared to native peptide (%) vs. GLP-1 | vs. Glucagon | vs. GIP |
|---|---|---|---|
| 21 | 0.1 | 1.6 | 0.2 |
| 22 | 0.1 | 0.9 | 0.5 |
| 42 | 3.1 | 23.1 | 1.2 |
| 43 | 2.1 | 13.5 | 0.6 |
| 50 | 15.4 | 6.9 | 0.7 |
| 77 | 6.7 | 1.7 | 6.6 |
| 96 | 0.3 | 4.0 | 0.3 |

The long-acting conjugates of triple agonists prepared above have the function of triple agonists which can activate all of GLP-1 receptors, GIP receptors, and glucagon receptors, and thus the long-acting conjugates of triple agonists can be used as a therapeutic material for treating patients with metabolic syndrome including diabetes and obesity.

Experimental Example 2: Measurement of In Vivo Activities of Long-Acting Conjugates of Triple Agonists In this experiment, high-fat diet-induced obesity mice, which are widely used as obesity animal models, were used. The body weight of the mice before administration was in a range of about 40 g to about 60 g. The mice were housed in group during the experiment and were given ad libitum access to water. Lighting was not provided between 6 AM and 6 PM.

The test groups fed with a high-fat diet include: Group 1, with an excipient (injection once every 2 days)—control group; Group 2, the long-acting conjugate of SEQ ID NO: 42 at 1.44 nmol/kg (injection once every 2 days); Group 3, the long-acting conjugate of SEQ ID NO: 42 at 2.88 nmol/kg (injection once every 2 days); Group 4, the long-acting conjugate of SEQ ID NO: 43 at 1.44 nmol/kg (injection once every 2 days); Group 5, the long-acting conjugate of SEQ ID NO: 43 at 2.88 nmol/kg (injection once every 2 days); Group 6, the long-acting conjugate of SEQ ID NO: 50 at 1.44 nmol/kg (injection once every 2 days); and Group 7, the long-acting conjugate of SEQ ID NO: 50 at 2.88 nmol/kg (injection once every 2 days). The experiment was terminated on the $28^{th}$ day, and the changes in body weight of the mice in each group were measured at 2-day intervals during the progress of the experiment. Upon termination of the experiment, the amount of mesenteric fat was measured by autopsy. Statistical analysis was performed to compare between the control group and test groups by 1-way ANOVA.

As a result of the measurement of changes in body weight, as can be confirmed in FIG. 1, all of the groups administered with a high-dose of the long-acting conjugate of SEQ ID NOS: 42, 43, and 50 showed a decrease in body weight by 56.9%, 57.0%, and 63.5%, respectively, compared to that before administration.

Additionally, as a result of the measurement of the amount of mesenteric fat, as can be confirmed in FIG. 2, all of the groups administered with a high-dose of the long-acting conjugate of SEQ ID NOS: 42, 43, and 50 showed a significant decrease in body fat, compared to the group administered with an excipient.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

The invention claimed is:

1. A conjugate of the following Chemical Formula (1):

X-La-F    Chemical Formula (1)

wherein

X is a peptide having activities to a glucagon receptor, a glucagon-like peptide-1 (GLP-1) receptor, and a glucose-dependent insulinotropic polypeptide (GIP) receptor;

L is a linker;

a is 0 or a positive integer, with the proviso that when a is 2 or greater, each L is independent from each other; and F is a material capable of increasing the half-life of X;

wherein the peptide comprises an amino acid sequence of the following Formula (3):

(SEQ ID NO: 105)
Xaa1-Xaa2-Gln-Gly-Thr-Phe-Thr-Ser-Asp-Tyr-Ser-Lys-

Xaa13-Leu-Asp-Glu-Xaa17-Xaa18-Xaa19-Lys-Xaa21-Phe-

Val-Xaa24-Trp-Leu-Leu-Xaa28-Xaa29-Xaa30-Xaa31-Ser-

Ser-Gly-Gln-Pro-Pro-Pro-Ser-Xaa40 wherein, in Formula (3),

Xaa1 is His or Tyr;

Xaa2 is α-methyl-glutamic acid or aminoisobutyric acid (Aib);

Xaa13 is Ala, Tyr, or Cys;

Xaa17 is Arg, Cys, or Lys;

Xaa18 is Ala or Arg;

Xaa19 is Ala or Cys;

Xaa21 is Glu or Asp;

Xaa24 is Gln or Asn;

Xaa28 is Cys or Asp;

Xaa29 is Cys, His, or Gln;

Xaa30 is Cys or His;

Xaa31 is Pro or Cys; and

Xaa40 is Cys or is absent.

2. The conjugate of claim 1, wherein X is a peptide comprising an amino acid sequence selected from the group consisting of SEQ ID NOS: 21, 22, 42, 43, 50, 64, 66, 67, 70, 71, 76, 77, 96, 97 and 100.

3. The conjugate according to claim 1, wherein, in Formula 3, the 16$^{th}$ amino acid and the 20$^{th}$ amino acid from the N-terminus together form a ring.

4. The conjugate of claim 1, wherein Xaa1 is Tyr.

5. A conjugate of the following Chemical Formula (1):

X-La-F    Chemical Formula (1)

wherein

X is a peptide having activities to a glucagon receptor, a glucagon-like peptide-1 (GLP-1) receptor, and a glucose-dependent insulinotropic polypeptide (GIP) receptor;

L is a linker;

a is 0 or a positive integer, with the proviso that when a is 2 or greater, each L is independent from each other; and F is a material capable of increasing the half-life of X;

wherein the peptide comprises an amino acid sequence of the following Formula (1):

(SEQ ID NO: 103)
Xaa1-Xaa2-Xaa3-Gly-Thr-Phe-Xaa7-Ser-Asp-Xaa10-Ser-

Xaa12-Xaa13-Xaa14-Xaa15-Xaa16-Xaa17-Xaa18-Xaa19-

Xaa20-Xaa21-Phe-Xaa23-Xaa24-Trp-Leu-Xaa27-Xaa28-

Xaa29-Xaa30-R1 wherein, in Formula (1),

Xaa1 is His, 4-imidazoacetyl (CA), or Tyr;

Xaa2 is α-methyl-glutamic acid, or aminoisobutyric acid (Aib);

Xaa3 is Gln;

Xaa7 is Thr;

Xaa10 is Tyr;

Xaa12 is Lys;

Xaa13 is Tyr, Ala, or Cys;

Xaa14 is Leu or Met;

Xaa15 is Cys, Asp, or Glu;

Xaa16 is Gly or Glu;

Xaa17 is Gln, Arg, Be, Glu, Cys, or Lys;

Xaa18 is Ala, Arg, or His;

Xaa19 is Ala, Gln, or Cys;

Xaa20 is Lys or Gln;

Xaa21 is Glu, Gln, Cys, or Asp;

Xaa23 is Ile or Val;

Xaa24 is Ala, Gln, Cys, or Asn;

Xaa27 is Leu or Lys;

Xaa28 is Cys, Lys, Ala, Asn, or Asp;

Xaa29 is Cys, Gly, Gln, Thr, Glu, or His;

Xaa30 is Cys, Gly, Lys, or His, or is absent; and

R1 is Cys, GKKNDWKHNIT (SEQ ID NO: 106), m-SS-GAPPPS-n (SEQ ID NO: 107), or m-SSGQPPPS-n (SEQ ID NO: 108), or is absent;

wherein m is -Cys-, -Pro-, or -Gly-Pro-; and n is -Cys-, -Gly-, -Ser-, or -His-Gly-, or is absent.

6. The conjugate of claim 5, wherein R1 is GKKND-WKHNIT (SEQ ID NO: 106).

7. The conjugate of claim 5, wherein X is a peptide comprising an amino acid sequence selected from the group consisting of SEQ ID NOS: 21 to 24, 27 to 32, 34, 36, 37, 39, 42, 43, 50 to 52, 56, 58, 64 to 71, 73 to 78, 81, 82, 86, 88, 89, 93, and 95 to 102.

8. The conjugate of claim 5, wherein X is a peptide comprising an amino acid sequence selected from the group consisting of SEQ ID NOS: 21, 22, 23, 31, 32, 42, 43, 50, 53, 55, 64 to 77, 79 and 96 to 102.

9. The conjugate of claim 5,
wherein, in Formula (1),
Xaa13 is Ala, Tyr, or Cys;
Xaa15 is Asp or Glu;
Xaa17 is Gln, Arg, Cys, or Lys;
Xaa18 is Ala, Arg, or His;
Xaa21 is Cys, Glu, or Asp;
Xaa23 is Ile or Val;
Xaa24 is Cys, Gln, or Asn;
Xaa28 is Cys, Asn, or Asp;
Xaa29 is Gln, Cys, or His; and
Xaa30 is Cys, Lys, or His.

10. The conjugate of claim 5,
wherein, in Formula (1),
Xaa1 is His or 4-imidazoacetyl;
Xaa13 is Ala or Cys;
Xaa14 is Met;
Xaa15 is Asp;
Xaa16 is Glu;
Xaa17 is Ile or Lys;
Xaa18 is Ala or His;
Xaa19 is Gln or Cys;
Xaa20 is Lys;
Xaa21 is Asp;
Xaa23 is Val;
Xaa24 is Asn;
Xaa28 is Ala or Asn;
Xaa29 is Gln or Thr; and
Xaa30 is Cys or Lys, or is absent.

11. The conjugate according to claim 1, wherein F is selected from the group consisting of a polymer, fatty acid, cholesterol, albumin and a fragment thereof, an albumin-binding material, a polymer of repeating units of particular amino acid sequences, an antibody, an antibody fragment, an FcRn-binding material, an in vivo connective tissue, a nucleotide, fibronectin, transferrin, a saccharide, heparin, and elastin.

12. The conjugate according to claim 11, wherein F is an immunoglobulin Fc region.

13. The conjugate according to claim 1, wherein L is a peptide, fatty acid, a saccharide, a polymer, a low molecular weight compound, a nucleotide, or a combination thereof.

14. The conjugate of claim 13, wherein the polymer is selected from the group consisting of polyethylene glycol, polypropylene glycol, an ethylene glycol-propylene glycol copolymer, polyoxyethylated polyol, polyvinyl alcohol, polysaccharide, dextran, polyvinyl ethyl ether, a biodegradable polymer, a lipid polymer, chitins, hyaluronic acid, an oligonucleotide, and a combination thereof.

15. A pharmaceutical composition comprising the conjugate of claim 1.

16. A method of treating metabolic syndrome comprising administering the conjugate according to claim 1 to a subject in need thereof.

17. The method of claim 16, wherein the metabolic syndrome comprises impaired glucose tolerance, hypercholesterolemia, dyslipidemia, obesity, diabetes, hypertension, arteriosclerosis due to dyslipidemia, atherosclerosis, arteriosclerosis, or coronary heart disease.

18. The conjugate according to claim 5, wherein F is selected from the group consisting of a polymer, fatty acid, cholesterol, albumin and a fragment thereof, an albumin-binding material, a polymer of repeating units of particular amino acid sequences, an antibody, an antibody fragment, an FcRn-binding material, an in vivo connective tissue, a nucleotide, fibronectin, transferrin, a saccharide, heparin, and elastin.

19. The conjugate according to claim 18, wherein F is an immunoglobulin Fc region.

20. The conjugate according to claim 5, wherein L is a peptide, fatty acid, a saccharide, a polymer, a low molecular weight compound, a nucleotide, or a combination thereof.

21. The conjugate of claim 20, wherein the polymer is selected from the group consisting of polyethylene glycol, polypropylene glycol, an ethylene glycol-propylene glycol copolymer, polyoxyethylated polyol, polyvinyl alcohol, polysaccharide, dextran, polyvinyl ethyl ether, a biodegradable polymer, a lipid polymer, chitins, hyaluronic acid, an oligonucleotide, and a combination thereof.

22. A pharmaceutical composition comprising the conjugate of claim 5.

23. A method of treating metabolic syndrome comprising administering the conjugate according to claim 5 to a subject in need thereof.

24. The method of claim 23, wherein the metabolic syndrome comprises impaired glucose tolerance, hypercholesterolemia, dyslipidemia, obesity, diabetes, hypertension, arteriosclerosis due to dyslipidemia, atherosclerosis, arteriosclerosis, or coronary heart disease.

* * * * *

UNITED STATES PATENT AND TRADEMARK OFFICE
CERTIFICATE OF CORRECTION

PATENT NO. : 10,400,020 B2
APPLICATION NO. : 16/024014
DATED : September 3, 2019
INVENTOR(S) : Euh Lim Oh et al.

Page 1 of 1

It is certified that error appears in the above-identified patent and that said Letters Patent is hereby corrected as shown below:

In the Claims

In Claim 5, Column 118, Line 51, delete "Be" and insert --Ile-- therefor.

Signed and Sealed this
Twenty-fourth Day of March, 2020

Andrei Iancu
*Director of the United States Patent and Trademark Office*

SEQUENCE LISTING

```
<160> NUMBER OF SEQ ID NOS: 118

<210> SEQ ID NO 1
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 1

His Xaa Gln Gly Thr Phe Thr Ser Asp Val Ser Ser Tyr Leu Asp Gly
 1               5                  10                  15

Gln Ala Ala Lys Glu Phe Ile Ala Trp Leu Val Lys Gly Cys
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 2

His Xaa Gln Gly Thr Phe Thr Ser Asp Val Ser Ser Tyr Leu Asp Gly
 1               5                  10                  15

Gln Ala Gln Lys Glu Phe Ile Ala Trp Leu Val Lys Gly Cys
            20                  25                  30

<210> SEQ ID NO 3
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 3

His Xaa Gln Gly Thr Phe Thr Ser Asp Val Ser Ser Tyr Leu Leu Gly
 1               5                  10                  15

Gln Ala Ala Lys Gln Phe Ile Ala Trp Leu Val Lys Gly Gly Gly Pro
            20                  25                  30

Ser Ser Gly Ala Pro Pro Pro Ser Cys
        35                  40

<210> SEQ ID NO 4
<211> LENGTH: 30
<212> TYPE: PRT
<213> ORGANISM: Artificial Sequence
<220> FEATURE:
<223> OTHER INFORMATION: Trigonal agonist
<220> FEATURE:
```

```
<221> NAME/KEY: MISC_FEATURE
<222> LOCATION: (2)
<223> OTHER INFORMATION: Xaa is aminoisobutyric acid (Aib)

<400> SEQUENCE: 4

His Xaa Gln Gly Thr Phe Thr Ser Asp Val Ser Ser Tyr Leu Leu Gly
1               5                   10                  15

Gln Gln Gln Lys Glu Phe Ile Ala Trp Leu Val Lys Gly Cys
            20                  25                  30

<210> SEQ ID NO 5
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 5

His Xaa Gln Gly Thr Phe Thr Ser Asp Val Ser Ser Tyr Leu Leu Gly
1               5                   10                  15

Gln Gln Gln Lys Glu Phe Ile Ala Trp Leu Val Lys Gly Gly Gly Pro
            20                  25                  30

Ser Ser Gly Ala Pro Pro Pro Ser Cys
        35                  40

<210> SEQ ID NO 6
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 6

His Xaa Gln Gly Thr Phe Thr Ser Asp Val Ser Ser Tyr Leu Asp Gly
1               5                   10                  15

Gln Ala Ala Lys Glu Phe Val Ala Trp Leu Leu Lys Gly Cys
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 7

His Xaa Gln Gly Thr Phe Thr Ser Asp Val Ser Lys Tyr Leu Asp Gly
1               5                   10                  15

Gln Ala Ala Lys Glu Phe Val Ala Trp Leu Leu Lys Gly Cys
            20                  25                  30

<210> SEQ ID NO 8
<211> LENGTH: 30
<212> TYPE: PRT
```

<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 8

His Xaa Gln Gly Thr Phe Thr Ser Asp Val Ser Lys Tyr Leu Asp Gly
1               5                   10                  15
Gln Ala Ala Gln Glu Phe Val Ala Trp Leu Leu Lys Gly Cys
            20                  25                  30

<210> SEQ ID NO 9
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 9

His Xaa Gln Gly Thr Phe Thr Ser Asp Val Ser Lys Tyr Leu Asp Gly
1               5                   10                  15
Gln Ala Ala Gln Glu Phe Val Ala Trp Leu Leu Ala Gly Cys
            20                  25                  30

<210> SEQ ID NO 10
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 10

His Xaa Gln Gly Thr Phe Thr Ser Asp Val Ser Lys Tyr Leu Asp Gly
1               5                   10                  15
Gln Ala Ala Gln Glu Phe Val Ala Trp Leu Leu Ala Gly Gly Pro
            20                  25                  30
Ser Ser Gly Ala Pro Pro Pro Ser Cys
        35                  40

<210> SEQ ID NO 11
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 11

Xaa Gly Glu Gly Thr Phe Thr Ser Asp Leu Ser Lys Tyr Leu Asp Ser
1               5                   10                  15
Arg Arg Gln Gln Leu Phe Val Gln Trp Leu Lys Ala Gly Gly Pro Ser
            20                  25                  30

Ser Gly Ala Pro Pro Pro Ser His Gly
        35                  40

<210> SEQ ID NO 12
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 12

Xaa Gly Glu Gly Thr Phe Ile Ser Asp Leu Ser Lys Tyr Met Asp Glu
1               5                   10                  15

Gln Ala Val Gln Leu Phe Val Glu Trp Leu Met Ala Gly Gly Pro Ser
            20                  25                  30

Ser Gly Ala Pro Pro Pro Ser His Gly
        35                  40

<210> SEQ ID NO 13
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 13

Xaa Gly Glu Gly Thr Phe Ile Ser Asp Tyr Ser Ile Gln Leu Asp Glu
1               5                   10                  15

Ile Ala Val Gln Asp Phe Val Glu Trp Leu Leu Ala Gln Lys Pro Ser
            20                  25                  30

Ser Gly Ala Pro Pro Pro Ser His Gly
        35                  40

<210> SEQ ID NO 14
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 14

Xaa Gly Gln Gly Thr Phe Thr Ser Asp Tyr Ser Ile Gln Leu Asp Glu
1               5                   10                  15

Ile Ala Val Arg Asp Phe Val Glu Trp Leu Lys Asn Gly Gly Pro Ser
            20                  25                  30

Ser Gly Ala Pro Pro Pro Ser His Gly
        35                  40

<210> SEQ ID NO 15
<211> LENGTH: 41
<212> TYPE: PRT
<213> ORGANISM: Artificial Sequence
<220> FEATURE:
<223> OTHER INFORMATION: Trigonal agonist

```
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 15

Xaa Gly Gln Gly Thr Phe Thr Ser Asp Leu Ser Lys Gln Met Asp Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser His Gly
        35                  40

<210> SEQ ID NO 16
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 16

Xaa Gly Gln Gly Thr Phe Thr Ser Asp Leu Ser Lys Gln Met Asp Ser
 1               5                  10                  15

Glu Ala Gln Gln Leu Phe Ile Glu Trp Leu Lys Asn Gly Gly Pro Ser
            20                  25                  30

Ser Gly Ala Pro Pro Pro Ser His Gly
        35                  40

<210> SEQ ID NO 17
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 17

Xaa Gly Gln Gly Thr Phe Thr Ser Asp Leu Ser Lys Gln Met Asp Glu
 1               5                  10                  15

Glu Arg Ala Arg Glu Phe Ile Glu Trp Leu Leu Ala Gln Lys Pro Ser
            20                  25                  30

Ser Gly Ala Pro Pro Pro Ser His Gly
        35                  40

<210> SEQ ID NO 18
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 18

Xaa Gly Gln Gly Thr Phe Thr Ser Asp Leu Ser Lys Gln Met Asp Ser
 1               5                  10                  15
```

```
Glu Arg Ala Arg Glu Phe Ile Glu Trp Leu Lys Asn Thr Gly Pro Ser
            20                  25                  30

Ser Gly Ala Pro Pro Pro Ser His Gly
        35                  40
```

<210> SEQ ID NO 19
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 19

```
Xaa Gly Gln Gly Thr Phe Thr Ser Asp Leu Ser Ile Gln Tyr Asp Ser
1               5                   10                  15

Glu His Gln Arg Asp Phe Ile Glu Trp Leu Lys Asp Thr Gly Pro Ser
            20                  25                  30

Ser Gly Ala Pro Pro Pro Ser His Gly
        35                  40
```

<210> SEQ ID NO 20
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 20

```
Xaa Gly Gln Gly Thr Phe Thr Ser Asp Leu Ser Ile Gln Tyr Glu Glu
1               5                   10                  15

Glu Ala Gln Gln Asp Phe Val Glu Trp Leu Lys Asp Thr Gly Pro Ser
            20                  25                  30

Ser Gly Ala Pro Pro Pro Ser His Gly
        35                  40
```

<210> SEQ ID NO 21
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 21

```
Tyr Xaa Gln Gly Thr Phe Thr Ser Asp Tyr Ser Lys Tyr Leu Asp Glu
1               5                   10                  15

Cys Arg Ala Lys Glu Phe Val Gln Trp Leu Leu Asp His His Pro Ser
            20                  25                  30

Ser Gly Gln Pro Pro Pro Ser
        35
```

```
<210> SEQ ID NO 22
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 22

Tyr Xaa Gln Gly Thr Phe Thr Ser Asp Tyr Ser Lys Cys Leu Asp Glu
1               5                   10                  15

Lys Arg Ala Lys Glu Phe Val Gln Trp Leu Leu Asp His His Pro Ser
            20                  25                  30

Ser Gly Gln Pro Pro Pro Ser
        35

<210> SEQ ID NO 23
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 23

Tyr Xaa Gln Gly Thr Phe Thr Ser Asp Tyr Ser Lys Tyr Leu Asp Glu
1               5                   10                  15

Cys Arg Ala Lys Glu Phe Val Gln Trp Leu Leu Ala Gln Lys Gly Lys
            20                  25                  30

Lys Asn Asp Trp Lys His Asn Ile Thr
        35                  40

<210> SEQ ID NO 24
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 24

Tyr Xaa Gln Gly Thr Phe Thr Ser Asp Tyr Ser Lys Tyr Leu Asp Glu
1               5                   10                  15

Cys Arg Ala Lys Glu Phe Val Gln Trp Leu Lys Asn Gly Gly Pro Ser
            20                  25                  30

Ser Gly Ala Pro Pro Pro Ser
```

<210> SEQ ID NO 25
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 25

His Xaa Gln Gly Thr Phe Thr Ser Asp Cys Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser
        35

<210> SEQ ID NO 26
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 26

His Xaa Gln Gly Thr Phe Thr Ser Asp Cys Ser Lys Tyr Leu Asp Ser
1               5                   10                  15

Arg Ala Ala Gln Asp Phe Val Gln Trp Leu Leu Asp Gly Gly Pro Ser
            20                  25                  30

Ser Gly Ala Pro Pro Pro Ser
        35

<210> SEQ ID NO 27
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 27

His Xaa Gln Gly Thr Phe Thr Ser Asp Tyr Ser Lys Tyr Leu Asp Glu
1               5                   10                  15

Arg Ala Cys Gln Asp Phe Val Gln Trp Leu Leu Asp Gln Gly Gly Pro
            20                  25                  30

Ser Ser Gly Ala Pro Pro Pro Ser
        35                  40

<210> SEQ ID NO 28
<211> LENGTH: 41
<212> TYPE: PRT
<213> ORGANISM: Artificial Sequence
<220> FEATURE:
<223> OTHER INFORMATION: Trigonal agonist
<220> FEATURE:

<221> NAME/KEY: MISC_FEATURE
<222> LOCATION: (2)
<223> OTHER INFORMATION: Xaa is aminoisobutyric acid (Aib)

<400> SEQUENCE: 28

His Xaa Gln Gly Thr Phe Thr Ser Asp Tyr Ser Lys Tyr Leu Asp Glu
1               5                   10                  15

Lys Arg Ala Gln Glu Phe Val Cys Trp Leu Leu Ala Gln Lys Gly Lys
            20                  25                  30

Lys Asn Asp Trp Lys His Asn Ile Thr
            35                  40

<210> SEQ ID NO 29
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 29

His Xaa Gln Gly Thr Phe Thr Ser Asp Tyr Ser Lys Tyr Leu Asp Glu
1               5                   10                  15

Lys Ala Ala Lys Glu Phe Val Gln Trp Leu Leu Asn Thr Cys
            20                  25                  30

<210> SEQ ID NO 30
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 30

His Xaa Gln Gly Thr Phe Thr Ser Asp Tyr Ser Lys Tyr Leu Asp Glu
1               5                   10                  15

Lys Ala Gln Lys Glu Phe Val Gln Trp Leu Leu Asp Thr Cys
            20                  25                  30

<210> SEQ ID NO 31
<211> LENGTH: 29
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 31

His Xaa Gln Gly Thr Phe Thr Ser Asp Tyr Ser Lys Tyr Leu Asp Glu
1               5                   10                  15

Lys Ala Cys Lys Glu Phe Val Gln Trp Leu Leu Ala Gln
            20                  25

<210> SEQ ID NO 32
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 32

His Xaa Gln Gly Thr Phe Thr Ser Asp Tyr Ser Lys Tyr Leu Asp Glu
1               5                   10                  15

Lys Ala Cys Lys Asp Phe Val Gln Trp Leu Leu Asp Gly Gly Pro Ser
            20                  25                  30

Ser Gly Ala Pro Pro Pro Ser
        35

<210> SEQ ID NO 33
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 33

His Xaa Gln Gly Thr Phe Thr Ser Asp Tyr Ser Ile Ala Met Asp Glu
1               5                   10                  15

Ile His Gln Lys Asp Phe Val Asn Trp Leu Leu Ala Gln Lys Cys
            20                  25                  30

<210> SEQ ID NO 34
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 34

His Xaa Gln Gly Thr Phe Thr Ser Asp Tyr Ser Lys Tyr Leu Asp Glu
1               5                   10                  15

```
Lys Arg Gln Lys Glu Phe Val Asn Trp Leu Leu Ala Gln Lys Cys
                20                  25                  30

<210> SEQ ID NO 35
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 35

His Xaa Gln Gly Thr Phe Thr Ser Asp Tyr Ser Ile Ala Met Asp Glu
 1               5                  10                  15

Ile His Gln Lys Asp Phe Val Asn Trp Leu Leu Asn Thr Lys Cys
                20                  25                  30

<210> SEQ ID NO 36
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 36

His Xaa Gln Gly Thr Phe Thr Ser Asp Tyr Ser Lys Tyr Leu Cys Glu
 1               5                  10                  15

Lys Arg Gln Lys Glu Phe Val Gln Trp Leu Leu Asn Gly Gly Pro Ser
                20                  25                  30

Ser Gly Ala Pro Pro Pro Ser Gly
        35                  40

<210> SEQ ID NO 37
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 37

His Xaa Gln Gly Thr Phe Thr Ser Asp Tyr Ser Lys Tyr Leu Asp Glu
 1               5                  10                  15

Cys Arg Gln Lys Glu Phe Val Gln Trp Leu Leu Asn Gly Gly Pro Ser
                20                  25                  30
```

-continued

Ser Gly Ala Pro Pro Pro Ser Gly
        35                  40

<210> SEQ ID NO 38
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 38

Xaa Xaa Gln Gly Thr Phe Thr Ser Asp Lys Ser Ser Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Ser
        35                  40

<210> SEQ ID NO 39
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 39

His Xaa Gln Gly Thr Phe Thr Ser Asp Tyr Ser Lys Tyr Leu Asp Gly
1               5                   10                  15

Gln His Ala Gln Cys Phe Val Ala Trp Leu Leu Ala Gly Gly Gly Pro
            20                  25                  30

Ser Ser Gly Ala Pro Pro Pro Ser
        35                  40

<210> SEQ ID NO 40
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 40

His Xaa Gln Gly Thr Phe Thr Ser Asp Lys Ser Lys Tyr Leu Asp Glu
1               5                   10                  15

Arg Ala Cys Gln Asp Phe Val Gln Trp Leu Leu Asp Gly Gly Pro Ser
            20                  25                  30

Ser Gly Ala Pro Pro Pro Ser
        35

<210> SEQ ID NO 41
<211> LENGTH: 39

```
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 41

His Xaa Gln Gly Thr Phe Thr Ser Asp Lys Ser Lys Tyr Leu Asp Glu
1               5                   10                  15

Cys Ala Ala Gln Asp Phe Val Gln Trp Leu Leu Asp Gly Gly Pro Ser
                20                  25                  30

Ser Gly Ala Pro Pro Pro Ser
        35

<210> SEQ ID NO 42
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 42

Tyr Xaa Gln Gly Thr Phe Thr Ser Asp Tyr Ser Lys Tyr Leu Asp Glu
1               5                   10                  15

Lys Arg Ala Lys Glu Phe Val Gln Trp Leu Leu Asp His His Pro Ser
                20                  25                  30

Ser Gly Gln Pro Pro Pro Ser Cys
        35                  40

<210> SEQ ID NO 43
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 43

Tyr Xaa Gln Gly Thr Phe Thr Ser Asp Tyr Ser Lys Tyr Leu Asp Glu
1               5                   10                  15

Lys Arg Ala Lys Glu Phe Val Gln Trp Leu Leu Asp His His Cys Ser
                20                  25                  30

Ser Gly Gln Pro Pro Pro Ser
        35

<210> SEQ ID NO 44
<211> LENGTH: 39
<212> TYPE: PRT
<213> ORGANISM: Artificial Sequence
```

-continued

```
<220> FEATURE:
<223> OTHER INFORMATION: Trigonal agonist

<400> SEQUENCE: 44

His Gly Gln Gly Thr Phe Thr Ser Asp Cys Ser Lys Gln Leu Asp Gly
1               5                   10                  15

Gln Ala Ala Gln Glu Phe Val Ala Trp Leu Leu Ala Gly Gly Pro Ser
            20                  25                  30

Ser Gly Ala Pro Pro Pro Ser
        35

<210> SEQ ID NO 45
<211> LENGTH: 39
<212> TYPE: PRT
<213> ORGANISM: Artificial Sequence
<220> FEATURE:
<223> OTHER INFORMATION: Trigonal agonist

<400> SEQUENCE: 45

His Gly Gln Gly Thr Phe Thr Ser Asp Cys Ser Lys Tyr Met Asp Gly
1               5                   10                  15

Gln Ala Ala Gln Asp Phe Val Ala Trp Leu Leu Ala Gly Gly Pro Ser
            20                  25                  30

Ser Gly Ala Pro Pro Pro Ser
        35

<210> SEQ ID NO 46
<211> LENGTH: 39
<212> TYPE: PRT
<213> ORGANISM: Artificial Sequence
<220> FEATURE:
<223> OTHER INFORMATION: Trigonal agonist

<400> SEQUENCE: 46

His Gly Gln Gly Thr Phe Thr Ser Asp Cys Ser Lys Tyr Leu Asp Glu
1               5                   10                  15

Gln His Ala Gln Glu Phe Val Ala Trp Leu Leu Ala Gly Gly Pro Ser
            20                  25                  30

Ser Gly Ala Pro Pro Pro Ser
        35

<210> SEQ ID NO 47
<211> LENGTH: 39
<212> TYPE: PRT
<213> ORGANISM: Artificial Sequence
<220> FEATURE:
<223> OTHER INFORMATION: Trigonal agonist

<400> SEQUENCE: 47

His Gly Gln Gly Thr Phe Thr Ser Asp Cys Ser Lys Tyr Leu Asp Gly
1               5                   10                  15

Gln Arg Ala Gln Glu Phe Val Ala Trp Leu Leu Ala Gly Gly Pro Ser
            20                  25                  30

Ser Gly Ala Pro Pro Pro Ser
        35

<210> SEQ ID NO 48
<211> LENGTH: 39
<212> TYPE: PRT
<213> ORGANISM: Artificial Sequence
<220> FEATURE:
<223> OTHER INFORMATION: Trigonal agonist
```

```
<400> SEQUENCE: 48

His Gly Gln Gly Thr Phe Thr Ser Asp Cys Ser Lys Tyr Leu Asp Gly
1               5                   10                  15

Gln Arg Ala Gln Asp Phe Val Asn Trp Leu Leu Ala Gly Gly Pro Ser
            20                  25                  30

Ser Gly Ala Pro Pro Ser
        35

<210> SEQ ID NO 49
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 49

Xaa Xaa Gln Gly Thr Phe Thr Ser Asp Tyr Ser Ile Cys Met Asp Glu
1               5                   10                  15

Ile His Gln Lys Asp Phe Val Asn Trp Leu Leu Asn Thr Lys
            20                  25                  30

<210> SEQ ID NO 50
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 50

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Leu Asp His His Pro Ser
            20                  25                  30

Ser Gly Gln Pro Pro Ser Cys
        35                  40

<210> SEQ ID NO 51
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
```

<222> LOCATION: (16)..(20)
<223> OTHER INFORMATION: amino acids at positions 16 and 20 form a ring

<400> SEQUENCE: 51

His Xaa Gln Gly Thr Phe Thr Ser Asp Tyr Ser Lys Tyr Leu Asp Glu
1               5                   10                  15

Lys Arg Gln Lys Glu Phe Val Gln Trp Leu Leu Asn Thr Cys
            20                  25                  30

<210> SEQ ID NO 52
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 52

His Xaa Gln Gly Thr Phe Thr Ser Asp Tyr Ser Lys Tyr Leu Asp Glu
1               5                   10                  15

Lys Arg Gln Lys Glu Phe Val Gln Trp Leu Leu Asp Thr Cys
            20                  25                  30

<210> SEQ ID NO 53
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 53

His Xaa Glu Gly Thr Phe Thr Ser Asp Tyr Ser Ile Ala Met Asp Glu
1               5                   10                  15

Ile His Gln Lys Asp Phe Val Asn Trp Leu Leu Ala Gln Cys
            20                  25                  30

<210> SEQ ID NO 54
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 54

His Xaa Glu Gly Thr Phe Thr Ser Asp Tyr Ser Ile Ala Met Asp Glu
1               5                   10                  15

Ile His Gln Lys Asp Phe Val Asp Trp Leu Leu Ala Glu Cys
            20                  25                  30

<210> SEQ ID NO 55
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 55

His Xaa Gln Gly Thr Phe Thr Ser Asp Tyr Ser Ile Ala Met Asp Glu
1               5                   10                  15

Ile His Gln Lys Asp Phe Val Asn Trp Leu Leu Ala Gln Cys
            20                  25                  30

<210> SEQ ID NO 56
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 56

His Xaa Gln Gly Thr Phe Thr Ser Asp Tyr Ser Lys Tyr Leu Asp Glu
1               5                   10                  15

Lys Arg Gln Lys Glu Phe Val Asn Trp Leu Leu Ala Gln Cys
            20                  25                  30

<210> SEQ ID NO 57
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 57

His Xaa Gln Gly Thr Phe Thr Ser Asp Tyr Ser Ile Ala Met Asp Glu
1               5                   10                  15

Ile His Gln Lys Asp Phe Val Asn Trp Leu Leu Asn Thr Cys
            20                  25                  30

<210> SEQ ID NO 58
<211> LENGTH: 31

```
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 58

His Xaa Gln Gly Thr Phe Thr Ser Asp Tyr Ser Lys Tyr Leu Asp Glu
1               5                   10                  15

Lys Arg Gln Lys Glu Phe Val Gln Trp Leu Leu Asn Thr Lys Cys
            20                  25                  30

<210> SEQ ID NO 59
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 59

Xaa Xaa Gln Gly Thr Phe Thr Ser Asp Tyr Ser Ile Cys Met Asp Glu
1               5                   10                  15

Lys His Gln Lys Asp Phe Val Asn Trp Leu Leu Asn Thr Lys
            20                  25                  30

<210> SEQ ID NO 60
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 60

Xaa Xaa Gln Gly Thr Phe Thr Ser Asp Tyr Ser Ile Ala Met Asp Glu
1               5                   10                  15

Lys His Cys Lys Asp Phe Val Asn Trp Leu Leu Asn Thr Lys
            20                  25                  30

<210> SEQ ID NO 61
```

-continued

```
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 61

Xaa Xaa Gln Gly Thr Phe Thr Ser Asp Tyr Ser Ile Ala Met Asp Glu
1               5                   10                  15

Ile Ala Cys Lys Asp Phe Val Asn Trp Leu Leu Asn Thr Lys
            20                  25                  30

<210> SEQ ID NO 62
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 62

Xaa Xaa Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser
        35

<210> SEQ ID NO 63
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 63

Xaa Xaa Gln Gly Thr Phe Thr Ser Asp Cys Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser
        35
```

<210> SEQ ID NO 64
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 64

Tyr Xaa Gln Gly Thr Phe Thr Ser Asp Tyr Ser Lys Tyr Leu Asp Glu
1               5                   10                  15

Cys Ala Ala Lys Glu Phe Val Gln Trp Leu Leu Asp His His Pro Ser
            20                  25                  30

Ser Gly Gln Pro Pro Pro Ser
        35

<210> SEQ ID NO 65
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 65

His Xaa Gln Gly Thr Phe Thr Ser Asp Tyr Ser Lys Cys Leu Asp Glu
1               5                   10                  15

Lys Arg Ala Lys Glu Phe Val Gln Trp Leu Leu Asp His His Pro Ser
            20                  25                  30

Ser Gly Gln Pro Pro Pro Ser
        35

<210> SEQ ID NO 66
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 66

Tyr Xaa Gln Gly Thr Phe Thr Ser Asp Tyr Ser Lys Tyr Leu Asp Glu
1               5                   10                  15

Cys Arg Ala Lys Asp Phe Val Gln Trp Leu Leu Asp His His Pro Ser
            20                  25                  30

Ser Gly Gln Pro Pro Pro Ser
        35

<210> SEQ ID NO 67
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 67

Tyr Xaa Gln Gly Thr Phe Thr Ser Asp Tyr Ser Lys Tyr Leu Asp Glu
1               5                   10                  15

Cys Ala Ala Lys Asp Phe Val Gln Trp Leu Leu Asp His His Pro Ser
            20                  25                  30

Ser Gly Gln Pro Pro Pro Ser
        35

<210> SEQ ID NO 68
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 68

Tyr Xaa Gln Gly Thr Phe Thr Ser Asp Tyr Ser Lys Cys Leu Asp Glu
1               5                   10                  15

Lys Ala Ala Lys Glu Phe Val Gln Trp Leu Leu Asp His His Pro Ser
            20                  25                  30

Ser Gly Gln Pro Pro Pro Ser
        35

<210> SEQ ID NO 69
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 69

Tyr Xaa Gln Gly Thr Phe Thr Ser Asp Tyr Ser Lys Cys Leu Asp Glu
1               5                   10                  15

Arg Ala Ala Lys Glu Phe Val Gln Trp Leu Leu Asp His His Pro Ser

Ser Gly Gln Pro Pro Pro Ser
         35

<210> SEQ ID NO 70
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 70

Tyr Xaa Gln Gly Thr Phe Thr Ser Asp Tyr Ser Lys Cys Leu Asp Glu
1               5                   10                  15

Lys Arg Ala Lys Asp Phe Val Gln Trp Leu Leu Asp His His Pro Ser
            20                  25                  30

Ser Gly Gln Pro Pro Pro Ser
         35

<210> SEQ ID NO 71
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 71

Tyr Xaa Gln Gly Thr Phe Thr Ser Asp Tyr Ser Lys Tyr Leu Asp Glu
1               5                   10                  15

Arg Ala Cys Lys Asp Phe Val Gln Trp Leu Leu Asp His His Pro Ser
            20                  25                  30

Ser Gly Gln Pro Pro Pro Ser
         35

<210> SEQ ID NO 72
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 72

Tyr Xaa Gln Gly Thr Phe Thr Ser Asp Cys Ser Lys Tyr Leu Asp Glu
1               5                   10                  15

```
Arg Ala Ala Lys Asp Phe Val Gln Trp Leu Leu Asp His His Pro Ser
            20                  25                  30

Ser Gly Gln Pro Pro Pro Ser
        35

<210> SEQ ID NO 73
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 73

Xaa Xaa Gln Gly Thr Phe Thr Ser Asp Tyr Ser Lys Tyr Leu Asp Glu
1               5                   10                  15

Cys Arg Ala Lys Glu Phe Val Gln Trp Leu Leu Asp His His Pro Ser
            20                  25                  30

Ser Gly Gln Pro Pro Pro Ser
        35

<210> SEQ ID NO 74
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 74

Xaa Xaa Gln Gly Thr Phe Thr Ser Asp Tyr Ser Lys Cys Leu Asp Glu
1               5                   10                  15

Lys Arg Ala Lys Glu Phe Val Gln Trp Leu Leu Asp His His Pro Ser
            20                  25                  30

Ser Gly Gln Pro Pro Pro Ser
        35

<210> SEQ ID NO 75
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
```

<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 75

Tyr Xaa Gln Gly Thr Phe Thr Ser Asp Tyr Ser Lys Tyr Leu Asp Glu
1               5                   10                  15

Lys Ala Ala Lys Glu Phe Val Gln Trp Leu Leu Asp His His Pro Ser
            20                  25                  30

Ser Gly Gln Pro Pro Pro Ser Cys
        35                  40

<210> SEQ ID NO 76
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 76

Tyr Xaa Gln Gly Thr Phe Thr Ser Asp Tyr Ser Lys Tyr Leu Asp Glu
1               5                   10                  15

Lys Arg Ala Lys Asp Phe Val Gln Trp Leu Leu Asp His His Pro Ser
            20                  25                  30

Ser Gly Gln Pro Pro Pro Ser Cys
        35                  40

<210> SEQ ID NO 77
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 77

Tyr Xaa Gln Gly Thr Phe Thr Ser Asp Tyr Ser Lys Tyr Leu Asp Glu
1               5                   10                  15

Lys Ala Ala Lys Asp Phe Val Gln Trp Leu Leu Asp His His Pro Ser
            20                  25                  30

Ser Gly Gln Pro Pro Pro Ser Cys
        35                  40

<210> SEQ ID NO 78
<211> LENGTH: 31
<212> TYPE: PRT
<213> ORGANISM: Artificial Sequence
<220> FEATURE:
<223> OTHER INFORMATION: Trigonal agonist
<220> FEATURE:

```
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 78

His Xaa Gln Gly Thr Phe Thr Ser Asp Tyr Ser Lys Tyr Leu Asp Glu
1               5                   10                  15

Lys Arg Gln Lys Glu Phe Val Gln Trp Leu Leu Asp Thr Lys Cys
                20                  25                  30

<210> SEQ ID NO 79
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 79

His Xaa Glu Gly Thr Phe Thr Ser Asp Tyr Ser Ile Ala Met Asp Glu
1               5                   10                  15

Ile His Gln Lys Asp Phe Val Asn Trp Leu Leu Ala Gln Lys Cys
                20                  25                  30

<210> SEQ ID NO 80
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 80

His Xaa Glu Gly Thr Phe Thr Ser Asp Tyr Ser Ile Ala Met Asp Glu
1               5                   10                  15

Ile His Gln Lys Asp Phe Val Asp Trp Leu Leu Ala Glu Lys Cys
                20                  25                  30

<210> SEQ ID NO 81
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
```

```
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 81

Xaa Xaa Gln Gly Thr Phe Thr Ser Asp Tyr Ser Lys Tyr Leu Asp Glu
1               5                   10                  15

Lys Arg Gln Lys Glu Phe Val Gln Trp Leu Leu Asn Thr Cys
            20                  25                  30

<210> SEQ ID NO 82
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 82

Xaa Xaa Gln Gly Thr Phe Thr Ser Asp Tyr Ser Lys Tyr Leu Asp Glu
1               5                   10                  15

Lys Arg Gln Lys Glu Phe Val Gln Trp Leu Leu Asp Thr Cys
            20                  25                  30

<210> SEQ ID NO 83
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 83

Xaa Xaa Glu Gly Thr Phe Thr Ser Asp Tyr Ser Ile Ala Met Asp Glu
1               5                   10                  15

Ile His Gln Lys Asp Phe Val Asn Trp Leu Leu Ala Gln Cys
            20                  25                  30

<210> SEQ ID NO 84
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
```

-continued

```
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 84

Xaa Xaa Glu Gly Thr Phe Thr Ser Asp Tyr Ser Ile Ala Met Asp Glu
1               5                   10                  15
Ile His Gln Lys Asp Phe Val Asp Trp Leu Leu Ala Glu Cys
            20                  25                  30

<210> SEQ ID NO 85
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 85

Xaa Xaa Gln Gly Thr Phe Thr Ser Asp Tyr Ser Ile Ala Met Asp Glu
1               5                   10                  15
Ile His Gln Lys Asp Phe Val Asn Trp Leu Leu Ala Gln Cys
            20                  25                  30

<210> SEQ ID NO 86
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 86

Xaa Xaa Gln Gly Thr Phe Thr Ser Asp Tyr Ser Lys Tyr Leu Asp Glu
1               5                   10                  15
Lys Arg Gln Lys Glu Phe Val Asn Trp Leu Leu Ala Gln Cys
            20                  25                  30

<210> SEQ ID NO 87
<211> LENGTH: 30
<212> TYPE: PRT
<213> ORGANISM: Artificial Sequence
```

```
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 87

Xaa Xaa Gln Gly Thr Phe Thr Ser Asp Tyr Ser Ile Ala Met Asp Glu
1               5                   10                  15

Ile His Gln Lys Asp Phe Val Asn Trp Leu Leu Asn Thr Cys
            20                  25                  30

<210> SEQ ID NO 88
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 88

Xaa Xaa Gln Gly Thr Phe Thr Ser Asp Tyr Ser Lys Tyr Leu Asp Glu
1               5                   10                  15

Lys Arg Gln Lys Glu Phe Val Gln Trp Leu Leu Asn Thr Lys Cys
            20                  25                  30

<210> SEQ ID NO 89
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 89

Xaa Xaa Gln Gly Thr Phe Thr Ser Asp Tyr Ser Lys Tyr Leu Asp Glu
1               5                   10                  15

Lys Arg Gln Lys Glu Phe Val Gln Trp Leu Leu Asp Thr Lys Cys
            20                  25                  30
```

```
<210> SEQ ID NO 90
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 90

Xaa Xaa Glu Gly Thr Phe Thr Ser Asp Tyr Ser Ile Ala Met Asp Glu
1               5                   10                  15
Ile His Gln Lys Asp Phe Val Asn Trp Leu Leu Ala Gln Lys Cys
            20                  25                  30

<210> SEQ ID NO 91
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 91

Xaa Xaa Glu Gly Thr Phe Thr Ser Asp Tyr Ser Ile Ala Met Asp Glu
1               5                   10                  15
Ile His Gln Lys Asp Phe Val Asp Trp Leu Leu Ala Glu Lys Cys
            20                  25                  30

<210> SEQ ID NO 92
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 92

Xaa Xaa Gln Gly Thr Phe Thr Ser Asp Tyr Ser Ile Ala Met Asp Glu
```

```
                1               5                  10                 15
Ile His Gln Lys Asp Phe Val Asn Trp Leu Leu Ala Gln Lys Cys
            20                  25                 30

<210> SEQ ID NO 93
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 93

Xaa Xaa Gln Gly Thr Phe Thr Ser Asp Tyr Ser Lys Tyr Leu Asp Glu
1               5                   10                  15
Lys Arg Gln Lys Glu Phe Val Asn Trp Leu Leu Ala Gln Lys Cys
            20                  25                  30

<210> SEQ ID NO 94
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 94

Xaa Xaa Gln Gly Thr Phe Thr Ser Asp Tyr Ser Ile Ala Met Asp Glu
1               5                   10                  15
Ile His Gln Lys Asp Phe Val Asn Trp Leu Leu Asn Thr Lys Cys
            20                  25                  30

<210> SEQ ID NO 95
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 95
```

Tyr Xaa Gln Gly Thr Phe Thr Ser Asp Tyr Ser Lys Tyr Leu Asp Glu
1               5                   10                  15

Lys Arg Ala Lys Glu Phe Val Gln Trp Leu Leu Cys His His Pro Ser
            20                  25                  30

Ser Gly Gln Pro Pro Pro Ser
        35

<210> SEQ ID NO 96
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 96

Tyr Xaa Gln Gly Thr Phe Thr Ser Asp Tyr Ser Lys Tyr Leu Asp Glu
1               5                   10                  15

Lys Arg Ala Lys Glu Phe Val Gln Trp Leu Leu Asp His Cys Pro Ser
            20                  25                  30

Ser Gly Gln Pro Pro Pro Ser
        35

<210> SEQ ID NO 97
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 97

Tyr Xaa Gln Gly Thr Phe Thr Ser Asp Tyr Ser Lys Tyr Leu Asp Glu
1               5                   10                  15

Lys Arg Ala Lys Glu Phe Val Gln Trp Leu Leu Asp Cys His Pro Ser
            20                  25                  30

Ser Gly Gln Pro Pro Pro Ser
        35

<210> SEQ ID NO 98
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 98

Tyr Xaa Gln Gly Thr Phe Thr Ser Asp Tyr Ser Lys Ala Leu Asp Glu
1               5                   10                  15

Lys Ala Ala Lys Glu Phe Val Asn Trp Leu Leu Asp His His Pro Ser
            20                  25                  30

Ser Gly Gln Pro Pro Pro Ser Cys
        35                  40

<210> SEQ ID NO 99
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 99

Tyr Xaa Gln Gly Thr Phe Thr Ser Asp Tyr Ser Lys Ala Leu Asp Glu
1               5                   10                  15

Lys Ala Ala Lys Asp Phe Val Asn Trp Leu Leu Asp His His Pro Ser
            20                  25                  30

Ser Gly Gln Pro Pro Pro Ser Cys
        35                  40

<210> SEQ ID NO 100
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 100

Tyr Xaa Gln Gly Thr Phe Thr Ser Asp Tyr Ser Lys Ala Leu Asp Glu
1               5                   10                  15

Lys Ala Ala Lys Glu Phe Val Gln Trp Leu Leu Asp Gln His Pro Ser
            20                  25                  30

Ser Gly Gln Pro Pro Pro Ser Cys
        35                  40

<210> SEQ ID NO 101
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)

<223> OTHER INFORMATION: amino acids at positions 16 and 20 form a ring

<400> SEQUENCE: 101

Tyr Xaa Gln Gly Thr Phe Thr Ser Asp Tyr Ser Lys Ala Leu Asp Glu
1               5                   10                  15
Lys Ala Ala Lys Glu Phe Val Asn Trp Leu Leu Asp Gln His Pro Ser
            20                  25                  30
Ser Gly Gln Pro Pro Pro Ser Cys
        35                  40

<210> SEQ ID NO 102
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 102

Tyr Xaa Gln Gly Thr Phe Thr Ser Asp Tyr Ser Lys Ala Leu Asp Glu
1               5                   10                  15
Lys Ala Ala Lys Asp Phe Val Asn Trp Leu Leu Asp Gln His Pro Ser
            20                  25                  30
Ser Gly Gln Pro Pro Pro Ser Cys
        35                  40

<210> SEQ ID NO 103
<211> LENGTH: 30
<212> TYPE: PRT
<213> ORGANISM: Artificial Sequence
<220> FEATURE:
<223> OTHER INFORMATION: General Formula 1
<220> FEATURE:
<221> NAME/KEY: MISC_FEATURE
<222> LOCATION: (1)
<223> OTHER INFORMATION: Xaa is His (H), 4-imidazoacetyl (CA), or Tyr
      (Y)
<220> FEATURE:
<221> NAME/KEY: MISC_FEATURE
<222> LOCATION: (2)
<223> OTHER INFORMATION: Xaa is Gly (G), alpha-methyl-glutamic acid, or
      Aib (aminoisobutyric acid)
<220> FEATURE:
<221> NAME/KEY: MISC_FEATURE
<222> LOCATION: (3)
<223> OTHER INFORMATION: Xaa is Glu (E) or Gln (Q)
<220> FEATURE:
<221> NAME/KEY: MISC_FEATURE
<222> LOCATION: (7)
<223> OTHER INFORMATION: Xaa is Thr (T) or Ile (I)
<220> FEATURE:
<221> NAME/KEY: MISC_FEATURE
<222> LOCATION: (10)
<223> OTHER INFORMATION: Xaa is Leu (L), Tyr (Y), Lys (K), Cys (C), or
      Val (V)
<220> FEATURE:
<221> NAME/KEY: MISC_FEATURE
<222> LOCATION: (12)
<223> OTHER INFORMATION: Xaa is Lys (K), Ser (S), or Ile (I)
<220> FEATURE:
<221> NAME/KEY: MISC_FEATURE
<222> LOCATION: (13)
<223> OTHER INFORMATION: Xaa is Gln (Q), Tyr (Y), Ala (A), or Cys (C)
<220> FEATURE:

```
<221> NAME/KEY: MISC_FEATURE
<222> LOCATION: (14)
<223> OTHER INFORMATION: Xaa is Leu (L), Met (M), or Tyr (Y)
<220> FEATURE:
<221> NAME/KEY: MISC_FEATURE
<222> LOCATION: (15)
<223> OTHER INFORMATION: Xaa is Cys (C), Asp (D), Glu (E), or Leu (L)
<220> FEATURE:
<221> NAME/KEY: MISC_FEATURE
<222> LOCATION: (16)
<223> OTHER INFORMATION: Xaa is Gly (G), Glu (E), or Ser (S)
<220> FEATURE:
<221> NAME/KEY: MISC_FEATURE
<222> LOCATION: (17)
<223> OTHER INFORMATION: Xaa is Gln (Q), Arg (R), Ile (I), Glu (E), Cys
      (C), or Lys (K)
<220> FEATURE:
<221> NAME/KEY: MISC_FEATURE
<222> LOCATION: (18)
<223> OTHER INFORMATION: Xaa is Ala (A), Gln (Q), Arg (R), or His (H)
<220> FEATURE:
<221> NAME/KEY: MISC_FEATURE
<222> LOCATION: (19)
<223> OTHER INFORMATION: Xaa is Ala (A), Gln (Q), Cys (C), or Val (V)
<220> FEATURE:
<221> NAME/KEY: MISC_FEATURE
<222> LOCATION: (20)
<223> OTHER INFORMATION: Xaa is Lys (K), Gln (Q), or Arg (R)
<220> FEATURE:
<221> NAME/KEY: MISC_FEATURE
<222> LOCATION: (21)
<223> OTHER INFORMATION: Xaa is Glu (E), Gln (Q), Leu (L), Cys (C), or
      Asp (D)
<220> FEATURE:
<221> NAME/KEY: MISC_FEATURE
<222> LOCATION: (23)
<223> OTHER INFORMATION: Xaa is Ile (I) or Val (V)
<220> FEATURE:
<221> NAME/KEY: MISC_FEATURE
<222> LOCATION: (24)
<223> OTHER INFORMATION: Xaa is Ala (A), Gln (Q), Cys (C), Asn (N), Asp
      (D), or Glu (E)
<220> FEATURE:
<221> NAME/KEY: MISC_FEATURE
<222> LOCATION: (27)
<223> OTHER INFORMATION: Xaa is Val (V), Leu (L), Lys (K), or Met (M)
<220> FEATURE:
<221> NAME/KEY: MISC_FEATURE
<222> LOCATION: (28)
<223> OTHER INFORMATION: Xaa is Cys (C), Lys (K), Ala (A), Asn (N), or
      Asp (D)
<220> FEATURE:
<221> NAME/KEY: MISC_FEATURE
<222> LOCATION: (29)
<223> OTHER INFORMATION: Xaa is Cys (C), Gly (G), Gln (Q), Thr (T), Glu
      (E), or His (H)
<220> FEATURE:
<221> NAME/KEY: MISC_FEATURE
<222> LOCATION: (30)
<223> OTHER INFORMATION: Xaa is Cys (C), Gly (G), Lys (K), or His (H),
      or is absent

<400> SEQUENCE: 103

Xaa Xaa Xaa Gly Thr Phe Xaa Ser Asp Xaa Ser Xaa Xaa Xaa Xaa Xaa
1               5                   10                  15

Xaa Xaa Xaa Xaa Xaa Phe Xaa Xaa Trp Leu Xaa Xaa Xaa Xaa
            20                  25                  30

<210> SEQ ID NO 104
<211> LENGTH: 40
<212> TYPE: PRT
<213> ORGANISM: Artificial Sequence
<220> FEATURE:
<223> OTHER INFORMATION: General Formula 2
<220> FEATURE:
<221> NAME/KEY: MISC_FEATURE
```

```
<222> LOCATION: (1)
<223> OTHER INFORMATION: Xaa is His (H), 4-imidazoacetyl (CA), or Tyr
      (Y)
<220> FEATURE:
<221> NAME/KEY: MISC_FEATURE
<222> LOCATION: (2)
<223> OTHER INFORMATION: Xaa is Gly (G), alpha-methyl-glutamic acid, or
      Aib (aminoisobutyric acid)
<220> FEATURE:
<221> NAME/KEY: MISC_FEATURE
<222> LOCATION: (10)
<223> OTHER INFORMATION: Xaa is Tyr (Y) or Cys (C)
<220> FEATURE:
<221> NAME/KEY: MISC_FEATURE
<222> LOCATION: (13)
<223> OTHER INFORMATION: Xaa is Gln (Q), Tyr (Y), Ala (A), or Cys (C)
<220> FEATURE:
<221> NAME/KEY: MISC_FEATURE
<222> LOCATION: (14)
<223> OTHER INFORMATION: Xaa is Leu (L), Met (M), or Tyr (Y)
<220> FEATURE:
<221> NAME/KEY: MISC_FEATURE
<222> LOCATION: (15)
<223> OTHER INFORMATION: Xaa is Asp (D), Glu (E), or Leu (L)
<220> FEATURE:
<221> NAME/KEY: MISC_FEATURE
<222> LOCATION: (16)
<223> OTHER INFORMATION: Xaa is Gly (G), Glu (E), or Ser (S)
<220> FEATURE:
<221> NAME/KEY: MISC_FEATURE
<222> LOCATION: (17)
<223> OTHER INFORMATION: Xaa is Gln (Q), Arg (R), Ile (I), Glu (E), Cys
      (C), or Lys (K)
<220> FEATURE:
<221> NAME/KEY: MISC_FEATURE
<222> LOCATION: (18)
<223> OTHER INFORMATION: Xaa is Ala (A), Gln (Q), Arg (R), or His (H)
<220> FEATURE:
<221> NAME/KEY: MISC_FEATURE
<222> LOCATION: (19)
<223> OTHER INFORMATION: Xaa is Ala (A), Gln (Q), Cys (C), or Val (V)
<220> FEATURE:
<221> NAME/KEY: MISC_FEATURE
<222> LOCATION: (20)
<223> OTHER INFORMATION: Xaa is Lys (K), Gln (Q), or Arg (R)
<220> FEATURE:
<221> NAME/KEY: MISC_FEATURE
<222> LOCATION: (21)
<223> OTHER INFORMATION: Xaa is Glu (E), Gln (Q), Leu (L), Cys (C), or
      Asp (D)
<220> FEATURE:
<221> NAME/KEY: MISC_FEATURE
<222> LOCATION: (23)
<223> OTHER INFORMATION: Xaa is Ile (I) or Val (V)
<220> FEATURE:
<221> NAME/KEY: MISC_FEATURE
<222> LOCATION: (24)
<223> OTHER INFORMATION: Xaa is Ala (A), Gln (Q), Cys (C), Asn (N), or
      Glu (E)
<220> FEATURE:
<221> NAME/KEY: MISC_FEATURE
<222> LOCATION: (28)
<223> OTHER INFORMATION: Xaa is Cys (C), Lys (K), Asn (N), or Asp (D)
<220> FEATURE:
<221> NAME/KEY: MISC_FEATURE
<222> LOCATION: (29)
<223> OTHER INFORMATION: Xaa is Cys (C), Gly (G), Gln (Q), or His (H)
<220> FEATURE:
<221> NAME/KEY: MISC_FEATURE
<222> LOCATION: (30)
<223> OTHER INFORMATION: Xaa is Cys (C), Gly (G), Lys (K), or His (H)
<220> FEATURE:
<221> NAME/KEY: MISC_FEATURE
<222> LOCATION: (31)
<223> OTHER INFORMATION: Xaa is Pro (P) or Cys (C)
<220> FEATURE:
<221> NAME/KEY: MISC_FEATURE
<222> LOCATION: (40)
<223> OTHER INFORMATION: Xaa is Cys (C), or is absent
```

<400> SEQUENCE: 104

Xaa Xaa Gln Gly Thr Phe Thr Ser Asp Xaa Ser Lys Xaa Xaa Xaa Xaa
1               5                   10                  15

Xaa Xaa Xaa Xaa Xaa Phe Xaa Xaa Trp Leu Leu Xaa Xaa Xaa Xaa Ser
            20                  25                  30

Ser Gly Gln Pro Pro Pro Ser Xaa
            35                  40

<210> SEQ ID NO 105
<211> LENGTH: 40
<212> TYPE: PRT
<213> ORGANISM: Artificial Sequence
<220> FEATURE:
<223> OTHER INFORMATION: General Formula 3
<220> FEATURE:
<221> NAME/KEY: MISC_FEATURE
<222> LOCATION: (1)
<223> OTHER INFORMATION: Xaa is His (H) or Tyr (Y)
<220> FEATURE:
<221> NAME/KEY: MISC_FEATURE
<222> LOCATION: (2)
<223> OTHER INFORMATION: Xaa is alpha-methyl-glutamic acid, or Aib
      (aminoisobutyric acid)
<220> FEATURE:
<221> NAME/KEY: MISC_FEATURE
<222> LOCATION: (13)
<223> OTHER INFORMATION: Xaa is Tyr (Y), Ala (A), or Cys (C)
<220> FEATURE:
<221> NAME/KEY: MISC_FEATURE
<222> LOCATION: (17)
<223> OTHER INFORMATION: Xaa is Arg (R), Cys (C), or Lys (K)
<220> FEATURE:
<221> NAME/KEY: MISC_FEATURE
<222> LOCATION: (18)
<223> OTHER INFORMATION: Xaa is Ala (A) or Arg (R)
<220> FEATURE:
<221> NAME/KEY: MISC_FEATURE
<222> LOCATION: (19)
<223> OTHER INFORMATION: Xaa is Ala (A) or Cys (C)
<220> FEATURE:
<221> NAME/KEY: MISC_FEATURE
<222> LOCATION: (21)
<223> OTHER INFORMATION: Xaa is Glu (E) or Asp (D)
<220> FEATURE:
<221> NAME/KEY: MISC_FEATURE
<222> LOCATION: (24)
<223> OTHER INFORMATION: Xaa is Gln (Q) or Asn (N)
<220> FEATURE:
<221> NAME/KEY: MISC_FEATURE
<222> LOCATION: (28)
<223> OTHER INFORMATION: Xaa is Cys (C) or Asp (D)
<220> FEATURE:
<221> NAME/KEY: MISC_FEATURE
<222> LOCATION: (29)
<223> OTHER INFORMATION: Xaa is Cys (C), Gln (Q), or His (H)
<220> FEATURE:
<221> NAME/KEY: MISC_FEATURE
<222> LOCATION: (30)
<223> OTHER INFORMATION: Xaa is Cys (C) or His (H)
<220> FEATURE:
<221> NAME/KEY: MISC_FEATURE
<222> LOCATION: (31)
<223> OTHER INFORMATION: Xaa is Pro (P) or Cys (C)
<220> FEATURE:
<221> NAME/KEY: MISC_FEATURE
<222> LOCATION: (40)
<223> OTHER INFORMATION: Xaa is Cys (C), or is absent

<400> SEQUENCE: 105

Xaa Xaa Gln Gly Thr Phe Thr Ser Asp Tyr Ser Lys Xaa Leu Asp Glu
1               5                   10                  15

Xaa Xaa Xaa Lys Xaa Phe Val Xaa Trp Leu Leu Xaa Xaa Xaa Xaa Ser

```
                20                  25                  30

Ser Gly Gln Pro Pro Ser Xaa
         35                  40

<210> SEQ ID NO 106
<211> LENGTH: 11
<212> TYPE: PRT
<213> ORGANISM: Artificial Sequence
<220> FEATURE:
<223> OTHER INFORMATION: R1

<400> SEQUENCE: 106

Gly Lys Lys Asn Asp Trp Lys His Asn Ile Thr
1               5                   10

<210> SEQ ID NO 107
<211> LENGTH: 8
<212> TYPE: PRT
<213> ORGANISM: Artificial Sequence
<220> FEATURE:
<223> OTHER INFORMATION: R1

<400> SEQUENCE: 107

Ser Ser Gly Ala Pro Pro Ser
1               5

<210> SEQ ID NO 108
<211> LENGTH: 8
<212> TYPE: PRT
<213> ORGANISM: Artificial Sequence
<220> FEATURE:
<223> OTHER INFORMATION: R1

<400> SEQUENCE: 108

Ser Ser Gly Gln Pro Pro Ser
1               5

<210> SEQ ID NO 109
<211> LENGTH: 9
<212> TYPE: PRT
<213> ORGANISM: Artificial Sequence
<220> FEATURE:
<223> OTHER INFORMATION: R1

<400> SEQUENCE: 109

Cys Ser Ser Gly Gln Pro Pro Ser
1               5

<210> SEQ ID NO 110
<211> LENGTH: 10
<212> TYPE: PRT
<213> ORGANISM: Artificial Sequence
<220> FEATURE:
<223> OTHER INFORMATION: R1

<400> SEQUENCE: 110

Gly Pro Ser Ser Gly Ala Pro Pro Ser
1               5                   10

<210> SEQ ID NO 111
<211> LENGTH: 11
<212> TYPE: PRT
<213> ORGANISM: Artificial Sequence
<220> FEATURE:
<223> OTHER INFORMATION: R1

<400> SEQUENCE: 111
```

Gly Pro Ser Ser Gly Ala Pro Pro Ser Cys
1               5                   10

<210> SEQ ID NO 112
<211> LENGTH: 9
<212> TYPE: PRT
<213> ORGANISM: Artificial Sequence
<220> FEATURE:
<223> OTHER INFORMATION: R1

<400> SEQUENCE: 112

Pro Ser Ser Gly Ala Pro Pro Pro Ser
1               5

<210> SEQ ID NO 113
<211> LENGTH: 10
<212> TYPE: PRT
<213> ORGANISM: Artificial Sequence
<220> FEATURE:
<223> OTHER INFORMATION: R1

<400> SEQUENCE: 113

Pro Ser Ser Gly Ala Pro Pro Pro Ser Gly
1               5                   10

<210> SEQ ID NO 114
<211> LENGTH: 11
<212> TYPE: PRT
<213> ORGANISM: Artificial Sequence
<220> FEATURE:
<223> OTHER INFORMATION: R1

<400> SEQUENCE: 114

Pro Ser Ser Gly Ala Pro Pro Pro Ser His Gly
1               5                   10

<210> SEQ ID NO 115
<211> LENGTH: 10
<212> TYPE: PRT
<213> ORGANISM: Artificial Sequence
<220> FEATURE:
<223> OTHER INFORMATION: R1

<400> SEQUENCE: 115

Pro Ser Ser Gly Ala Pro Pro Pro Ser Ser
1               5                   10

<210> SEQ ID NO 116
<211> LENGTH: 9
<212> TYPE: PRT
<213> ORGANISM: Artificial Sequence
<220> FEATURE:
<223> OTHER INFORMATION: R1

<400> SEQUENCE: 116

Pro Ser Ser Gly Gln Pro Pro Pro Ser
1               5

<210> SEQ ID NO 117
<211> LENGTH: 10
<212> TYPE: PRT
<213> ORGANISM: Artificial Sequence
<220> FEATURE:
<223> OTHER INFORMATION: R1

<400> SEQUENCE: 117

```
Pro Ser Ser Gly Gln Pro Pro Pro Ser Cys
1               5                   10

<210> SEQ ID NO 118
<211> LENGTH: 29
<212> TYPE: PRT
<213> ORGANISM: Homo sapiens

<400> SEQUENCE: 118

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25
```